(12) United States Patent
Steinhagen et al.

(10) Patent No.: US 8,097,758 B2
(45) Date of Patent: Jan. 17, 2012

(54) ISOSERINE DERIVATIVES FOR USE AS COAGULATION FACTOR IXA INHIBITORS

(75) Inventors: Henning Steinhagen, Sulzbach (DE); Markus Follmann, Wulfrath (DE); Jochen Goerlitzer, Frankfurt am Main (DE); Herman Schreuder, Hofheim (DE)

(73) Assignee: Sanofi-Aventis, Paris (FR)

( * ) Notice: Subject to any disclaimer, the term of this patent is extended or adjusted under 35 U.S.C. 154(b) by 501 days.

(21) Appl. No.: 12/400,189

(22) Filed: Mar. 9, 2009

(65) Prior Publication Data

US 2009/0233949 A1 Sep. 17, 2009

Related U.S. Application Data

(63) Continuation of application No. PCT/EP2007/007613, filed on Aug. 31, 2007.

(30) Foreign Application Priority Data

Sep. 13, 2006 (DE) .......... 10 2006 042 926

(51) Int. Cl.
| | |
|---|---|
| C07C 233/65 | (2006.01) |
| C07C 233/05 | (2006.01) |
| C07D 217/22 | (2006.01) |
| C07D 277/82 | (2006.01) |
| C07D 239/72 | (2006.01) |
| A61K 31/16 | (2006.01) |
| A61K 31/4184 | (2006.01) |
| A61K 31/428 | (2006.01) |
| A61K 31/47 | (2006.01) |

(52) U.S. Cl. ............ 564/158; 548/163; 548/307.4; 546/143; 514/310; 514/367; 514/395; 514/616

(58) Field of Classification Search .......... 546/143; 548/163, 307.4; 564/158; 514/310, 367, 514/395, 616
See application file for complete search history.

(56) References Cited

U.S. PATENT DOCUMENTS

| | | | |
|---|---|---|---|
| 5,633,268 | A | 5/1997 | Kirstgen et al. |
| 6,297,269 | B1 | 10/2001 | Hulin et al. |
| 2001/0006977 | A1 | 7/2001 | Ries et al. |
| 2005/0137168 | A1 | 6/2005 | Gobbi et al. |
| 2009/0105231 | A1* | 4/2009 | Sawada et al. ............ 514/227.8 |

FOREIGN PATENT DOCUMENTS

| | | |
|---|---|---|
| DE | 42 38 260 A1 | 5/1994 |
| WO | WO 94/22885 | 10/1994 |
| WO | WO 02/42273 A2 | 5/2002 |
| WO | WO 2004/072101 A2 | 8/2004 |

OTHER PUBLICATIONS

Weltermann et al, The risk of recurrent venous thromboembolism among patients with high factor IX levels, J. Thromb. and Haemost. 2003 (1) pp. 28-32.
Batt et. al., 5-Amidinoindoles as Dual Inhibitors of Coagulation Factors IXa and Xa, Bioorganic & Medicinal Chemistry Letters, vol. 14, (2004), pp. 5269-5273.
Feuerstein et al, an Inhibitory Anti-factor IX Antibody Effectively Reduces Thrombus Formation in a Rat Model of Venous Thrombosis, Thromb. Haemost. 1999 (82) pp. 1443-1445.
Sharpless et al, N-Bromoacetamide—A New Nitrogen Source for the Catalytic Asymmetric Aminohydroxylation of Olefins, Angew. Chem. Int. Ed. Engl 1997 (36) 13|14 pp. 1483-1486.

* cited by examiner

*Primary Examiner* — Shailendra Kumar
(74) *Attorney, Agent, or Firm* — Scully, Scott, Murphy & Presser, P.C.

(57) ABSTRACT

The invention relates to the compounds of formula (I)

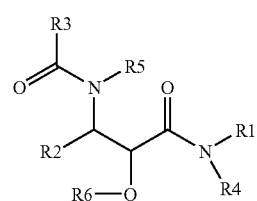

(I)

having antithrombotic activity which especially inhibit blood clotting factor IXa, to methods for producing the same and to the use thereof as drugs.

8 Claims, No Drawings

ISOSERINE DERIVATIVES FOR USE AS COAGULATION FACTOR IXA INHIBITORS

This application is a CON of PCT/EP2007/007613, filed Aug. 31, 2007.

The invention relates to novel compounds of the formula I having antithrombotic activity which, in particular, inhibit blood clotting factor IXa, to processes for their preparation and to use thereof as medicaments.

Blood clotting is a process of control of the blood stream essential for the survival of mammals. The process of clotting and the subsequent dissolution of the clot after wound healing has taken place commences after vascular damage and can be divided into four phases:
1. The phase of vasoconstriction or vasocontraction: By means of this the blood loss in the damaged area is decreased.
2. The next phase is platelet activation by thrombin. The platelets attach to the site of the vessel wall damage and form a platelet aggregate. The protein fibrinogen is responsible here for the crosslinkage of the platelets by means of appropriate surface receptors. Platelets also bind to exposed collagen of the extracellular matrix of the damaged vessel wall and are activated by this means. After activation of the platelets, a number of messenger substances are secreted, which induce the activation of further platelets. At the same time, a membrane lipid, phosphatidylserine, is transported from the inside of the membrane of the platelets to the outside, on which complexes of clotting factors can accumulate. The platelets accelerate blood clotting by means of this mechanism.
3. The formation of these clotting complexes leads to the massive formation of thrombin, which converts soluble fibrinogen to fibrin by cleavage of two small peptides. Fibrin monomers spontaneously form threadlike strands, from which, after crosslinkage by clotting factor XIII, a stable protein network forms. The initially even looser platelet aggregate is stabilized by this fibrin network; platelet aggregates and fibrin network are the two essential constituents of a thrombus.
4. After wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors.

The intrinsic pathway requires the clotting factors V, VIII, IX, X, XI and XII and also prekallikrein, high molecular weight kininogen, calcium ions and phospholipids from platelets.

The intrinsic pathway is initiated when prekallikrein, high molecular weight kininogen factor XI and XII bind to a negatively charged surface. This point in time is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, such that activation is the result. With increasing activation of factor XII, activation of factor XI occurs, which leads to a release of bradykinin, a vasodilator. As a result, the ending of the initial phase of vasoconstriction occurs. Bradykinin is formed from high molecular weight kininogen. In the presence of $Ca^{2+}$ ions, factor XIa activates factor IX. Factor IX is a proenzyme, which contains vitamin K-dependent, γ-carboxyglutamic acid (GLA) residues. The serine protease activity becomes noticeable after binding of $Ca^{2+}$ to these GLA residues. A number of the serine proteases of the blood clotting cascade (factors II, VII, IX and X) contain such vitamin K-dependent GLA residues. Factor IXa cleaves factor X and leads to activation to factor Xa. The prerequisite for the formation of factor IXa is the formation of a tenase complex from $Ca^{2+}$ and the factors VIIIa, IXa and X on the surface of activated platelets. One of the reactions of activated platelets is the presentation of phosphatidylserine and phosphatidylinositol along the surfaces. The exposure of these phospholipids first makes the formation of the tenase complex possible. Factor VIII in this process has the function of a receptor for the factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further and inactivated by thrombin. This dual activity of thrombin in relation to factor VIII leads to a self-restriction of tenase complex formation and thus to a limitation of blood clotting.

The extrinsic pathway requires a tissue factor (TF) and clotting factors V, VII, VIII, IX and X. In the case of a vessel injury, the tissue factor (TF) accumulates with the clotting factor VII and the latter is activated. The complex of TF and clotting factor VII has two substrates, clotting factors X and IX.

Clotting factor IX can be activated by means of the intrinsic pathway and the extrinsic pathway. The activation of factor IXa is thus a central point of intersection between the two pathways of activation of clotting.

Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445).

The compounds of the formula I according to the invention are suitable for prophylactic and for therapeutic administration to humans who suffer from diseases which accompany thromboses, embolisms, hypercoaguability or fibrotic changes. They can be employed for secondary prevention and are suitable both for acute and for long-term therapy.

The invention therefore relates to a compound of the formula I

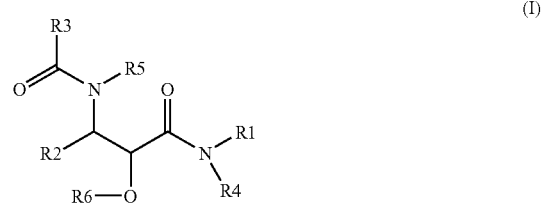

and/or all stereoisomeric forms of the compound of the formula I and/or mixtures of these forms in any ratio, and/or a physiologically tolerable salt of the compound of the formula I, where R1 is
1) —$(C_6-C_{14})$-aryl-Z, in which Z is a basic nitrogen-containing group and in which aryl is unsubstituted or mono-, di- or trisubstituted by T,
2) —$(C_3-C_{12})$-cycloalkyl-Z, in which Z is a basic nitrogen-containing group and in which cycloalkyl is unsubstituted or mono-, di- or trisubstituted by T,
3) a four- to fifteen-membered Het-Z, in which Z is a basic nitrogen-containing group and in which Het is unsubstituted or additionally mono-, di- or trisubstituted by T, R2 is
1) —$(C_0-C_4)$-alkylene-$(C_6-C_{14})$-aryl, in which aryl is unsubstituted or mono-, di- or trisubstituted by T,
2) —$(C_0-C_4)$-alkylene-$(C_3-C_8)$-cycloalkyl, in which cycloalkyl is unsubstituted or mono-, di- or trisubstituted by T, or
3) —$(C_0-C_4)$-alkylene-Het, in which Het is unsubstituted or mono-, di- or trisubstituted by T, R3 is
1) —$(C_0-C_4)$-alkylene-$(C_6-C_{14})$-aryl, in which aryl is unsubstituted or mono-, di- or trisubstituted by T,
2) —O—$(C_1-C_4)$-alkylene-$(C_6-C_{14})$-aryl, in which aryl is unsubstituted or mono-, di- or trisubstituted by T,
3) —$(C_0-C_4)$-alkylene-Het, in which Het is unsubstituted or mono-, di- or trisubstituted by T,
4) —O—$(C_1-C_4)$-alkylene-Het, in which Het is unsubstituted or mono-, di- or trisubstituted by T,
5) —$(C_0-C_4)$-alkylene-$(C_6-C_{14})$-aryl-Q-$(C_6-C_{14})$-aryl, in which the two aryl radicals in each case independently of one another are unsubstituted or mono-, di- or trisubstituted by T,
6) —$(C_0-C_4)$-alkylene-$(C_6-C_{14})$-aryl-Q-$(C_3-C_{12})$-cycloalkyl, in which aryl and cycloalkyl in each case independently of one another are unsubstituted or mono-, di- or trisubstituted by T,
7) —$(C_0-C_4)$-alkylene-$(C_6-C_{14})$-aryl-Q-Het, in which aryl and Het in each case independently of one another are unsubstituted or mono-, di- or trisubstituted by T,
8) —$(C_0-C_4)$-alkylene-Het-Q-$(C_6-C_{14})$-aryl, in which aryl and Het in each case independently of one another are unsubstituted or mono-, di- or trisubstituted by T, or
9) —$(C_0-C_4)$-alkylene-Het-Q-Het, in which the two Het radicals in each case independently of one another are unsubstituted or mono-, di- or trisubstituted by T,
10) —N(R5)—$(C_1-C_4)$-alkylene-$(C_6-C_{14})$-aryl, in which aryl is unsubstituted or mono-, di- or trisubstituted by T, or
11) —N(R5)—$(C_1-C_4)$-alkylene-Het, in which Het is unsubstituted or mono-, di- or trisubstituted by T, Q is a covalent bond, —$(C_1-C_4)$-alkylene, —NH—, —N($(C_1-C_4)$-alkyl)-, —O—, —S—, or —$SO_2$—, T is
1) halogen,
2) —$(C_1-C_6)$-alkyl, in which alkyl is unsubstituted or mono-, di- or trisubstituted by —$(C_1-C_3)$-fluoroalkyl, —N—C(O)—OH or —N—C(O)—$(C_1-C_4)$—alkyl,
3) —$(C_1-C_3)$-fluoroalkyl,
4) —$(C_3-C_9)$-cycloalkyl,
5) —OH,
6) —O—$(C_1-C_4)$-alkyl,
7) —O—$(C_1-C_3)$-fluoroalkyl,
8) —$NO_2$,
9) —CN,
10) —N(R10)(R11), in which R10 and R11 independently of one another are a hydrogen atom, —$(C_3-C_8)$-cycloalkyl, halogen or —$(C_1-C_6)$-alkyl,
11) —C(O)—NH—R10,
12) —NH—C(O)—R10,
13) —NH—$SO_2$—R10,
14) —$SO_2$—$(C_1-C_4)$-alkyl,
15) —$SO_2$—NH—R10,
16) —$SO_2$—$(C_1-C_3)$-fluoroalkyl,
17) —S—$(C_1-C_4)$-alkyl or
18) —S—$(C_1-C_3)$-fluoroalkyl, R4 and R5 are identical or different and independently of one another are a hydrogen atom or —$(C_1-C_4)$-alkyl, and R6 is a hydrogen atom, —C(O)—R12, —C(O)—O—R12, —C(O)—NH—R12 or —$(C_1-C_4)$-alkyl, where R12 is —$(C_1-C_6)$-alkyl, —$(C_3-C_8)$-cycloalkyl, —$(C_6-C_{14})$-aryl or Het.

The invention further relates to a compound of the formula I and/or all stereoisomeric forms of the compound of the formula I and/or mixtures of these forms in any ratio, and/or a physiologically tolerable salt of the compound of the formula I, where R1 is
1) —$(C_6-C_{14})$-aryl-Z, where aryl is selected from the group consisting of phenyl and naphthyl, and in which aryl is unsubstituted or mono-, di- or trisubstituted by T and Z is amino, amidino, aminomethylene, aminopyridinyl, azetidinyl, guanidino, piperidinyl, pyridinyl or pyrrolidinyl, or
2) a four- to fifteen-membered Het-Z, where Het is selected from the group consisting of acridinyl, azepinyl, azetidinyl, benzimidazolinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, beta-carbolinyl, quinazolinyl, quinolinyl, quinolizinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl or xanthenyl and in which Het is unsubstituted or mono-, di- or trisubstituted by T and in which Z is as defined above, R2 is
1) —($C_0$-$C_4$)-alkylene-($C_6$-$C_{14}$)-aryl, in which aryl is as defined above and is unsubstituted or mono-, di- or trisubstituted by T,
2) —($C_0$-$C_4$)-alkylene-($C_3$-$C_8$)-cycloalkyl, in which cycloalkyl is unsubstituted or mono-, di- or trisubstituted by T, or
3) —($C_0$-$C_4$)-alkylene-Het, in which Het is as defined above and is unsubstituted or mono-, di- or trisubstituted by T, R3 is
1) —($C_0$-$C_4$)-alkylene-($C_6$-$C_{14}$)-aryl, in which aryl is as defined above and is unsubstituted or mono-, di- or trisubstituted by T,
2) —($C_0$-$C_4$)-alkylene-Het, in which Het is as defined above and is unsubstituted or mono-, di- or trisubstituted by T,
3) —($C_0$-$C_4$)-alkylene-($C_6$-$C_{14}$)-aryl-Q-($C_6$-$C_{14}$)-aryl, in which the two aryls in each case independently of one another are as defined above and in each case independently of one another are unsubstituted or mono-, di- or trisubstituted by T,
4) —($C_0$-$C_4$)-alkylene-($C_6$-$C_{14}$)-aryl-Q-($C_3$-$C_{12}$)-cycloalkyl, in which aryl is as defined above and cycloalkyl is unsubstituted or mono-, di- or trisubstituted by T,
5) —($C_0$-$C_4$)-alkylene-($C_6$-$C_{14}$)-aryl-Q-Het, in which aryl and Het are as defined above and in each case independently of one another are unsubstituted or mono-, di- or trisubstituted by T,
6) —($C_0$-$C_4$)-alkylene-Het-Q-($C_6$-$C_{14}$)-aryl, in which aryl and Het are as defined above and in each case independently of one another are unsubstituted or mono-, di- or trisubstituted by T, or
7) —($C_0$-$C_4$)-alkylene-Het-Q-Het, in which the two Het radicals are as defined above and in each case independently of one another are unsubstituted or mono-, di- or trisubstituted by T, Q is a covalent bond, —($C_1$-$C_4$)-alkylene, —NH—, —N(($C_1$-$C_4$)-alkyl)- or —O—, T is
1) halogen,
2) —($C_1$-$C_6$)-alkyl, in which alkyl is unsubstituted or is mono-, di- or trisubstituted by —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_6$)-cycloalkyl,
5) —OH, 6) —O—($C_1$-$C_4$)-alkyl,
7) —O—($C_1$-$C_3$)-fluoroalkyl,
8) —$NO_2$,
9) —CN,
10) —N(R10)(R11), in which R10 and R11 independently of one another are a hydrogen atom, —($C_3$-$C_6$)-cycloalkyl, halogen or —($C_1$-$C_6$)-alkyl,
11) —C(O)—NH—R10,
12) —NH—C(O)—R10,
13) —NH—$SO_2$—R10,
14) —$SO_2$—($C_1$-$C_4$)-alkyl,
15) —$SO_2$—NH—R10,
16) —$SO_2$—($C_1$-$C_3$)-fluoroalkyl,
17) —S—($C_1$-$C_4$)-alkyl or
18) —S—($C_1$-$C_3$)-fluoroalkyl, R4 and R5 are identical or different and independently of one another are a hydrogen atom or —($C_1$-$C_4$)-alkyl, and R6 is a hydrogen atom, —C(O)—R12, —C(O)—O—R12, —C(O)—NH—R12 or —($C_1$-$C_4$)-alkyl, where R12 is —($C_1$-$C_6$)-alkyl, —($C_3$-$C_6$)-cycloalkyl, —($C_6$-$C_{14}$)-aryl or Het.

The invention furthermore relates to a compound of the formula I and/or all stereoisomeric forms of the compound of the formula I and/or mixtures of these forms in any ratio, and/or a physiologically tolerable salt of the compound of the formula I, where R1 is 4-benzamidine, aminomethylphenyl or Het-Z, where Het is selected from the group consisting of benzimidazolyl, benzothiazolyl and isoquinolinyl, and in which Z is amino, R2 is
1) phenyl, in which phenyl is unsubstituted or mono- or disubstituted by T, or
2) Het-1, in which Het-1 is selected from the group consisting of furanyl, pyrazolyl or thienyl and Het-1 is unsubstituted or mono- or disubstituted by T, R3 is
1) phenyl, in which phenyl is unsubstituted or mono- or disubstituted by T,
2) Het-2, in which Het-2 is selected from the group consisting of benzimidazolyl, benzofuranyl, benzothiophenyl, quinolinyl, quinoxalinyl, furanyl, indolyl, isoquinolinyl, isoxazolyl, morpholinyl, piperidinyl, pyridyl, pyrimidinyl, pyrrolidinyl, pyrrolyl, thienyl, thienopyrrolyl or thienothiophenyl and in which Het-2 is unsubstituted or mono- or disubstituted by T,
3) -phenyl-Q-phenyl, in which the two phenyl radicals in each case independently of one another are unsubstituted or mono- or disubstituted by T,
4) phenyl-Q-($C_3$-$C_6$)-cycloalkyl, in which phenyl and cycloalkyl in each case independently of one another are unsubstituted or mono- or disubstituted by T,
5) phenyl-Q-Het-2, in which Het-2 is as defined above and phenyl and Het-2 in each case independently of one another are unsubstituted or mono- or disubstituted by T,
6) Het-2-Q-phenyl, in which Het-2 is as defined above and phenyl and Het-2 in each case independently of one another are unsubstituted or mono- or disubstituted by T, or
7) Het-2-Q-Het-2, in which the two Het-2 radicals are as defined above and in each case independently of one another are unsubstituted or mono- or disubstituted by T, Q is a covalent bond, —$CH_2$—, —N($CH_3$)— or —O—, T is
1) F, Cl or Br,
2) —($C_1$-$C_4$)-alkyl, in which alkyl is unsubstituted or mono- or disubstituted by —$CF_3$ or —N—C(O)—$CH_3$,
3) —$CF_3$,
4) —O—($C_1$-$C_4$)-alkyl,
5) —O—$CF_3$,
6) —$NO_2$,
7) —N(R10)(R11), in which R10 and R11 independently of one another are a hydrogen atom or —($C_1$-$C_4$)-alkyl,
8) —$SO_2$—$CH_3$,
9) —S—$CF_3$ or
10) —S—($C_1$-$C_2$)-alkyl, R4, R5 and R6 are in each case a hydrogen atom.

The term "($C_1$-$C_4$)-alkyl" or "($C_1$-$C_6$)-alkyl" is understood as meaning hydrocarbon radicals whose carbon chain is straight-chain or branched and contains 1 to 4 or 1 to 6 carbon atoms, for example methyl, ethyl, propyl, isopropyl, butyl, isobutyl, tertiary-butyl, pentyl, isopentyl, neopentyl, hexyl, 2,3-dimethylbutane or neohexyl.

The term "—(C$_0$-C$_4$)-alkylene" is understood as meaning hydrocarbon radicals whose carbon chain is straight-chain or branched and contains 1 to 4 carbon atoms, for example methylene, ethylene, propylene, isopropylene, isobutylene, butylene or tertiary-butylene. "—C$_0$-Alkylene" is a covalent bond. The term "—(C$_1$-C$_4$)-alkylene" is understood as meaning hydrocarbon radicals whose carbon chain is straight-chain or branched and contains 1 to 4 carbon atoms, for example methylene (—CH$_2$—), ethylene (—CH$_2$—CH$_2$—), propylene (—CH$_2$—CH$_2$—CH$_2$—), isopropylene, isobutylene, butylene or tertiary-butylene.

The term "—(C$_3$-C$_{12}$)-cycloalkyl" is understood as meaning rings of 3 to 12 carbon atoms such as compounds which are derived from monocycles having 3 to 8 carbon atoms in the ring such as cyclopropane, cyclobutane, cyclopentane, cyclohexane, cycloheptane or cyclooctane, which are derived from the bicycles bicyclo[4.2.0]octane, octahydroindene, decahydronaphthalene, decahydroazulene, decahydrobenzocycloheptene or dodecahydroheptalene or from the bridged cycles such as spiro[2.5]octane, spiro[3.4]octane, spiro[3.5]nonane, bicyclo[3.1.1]heptane, bicyclo[2.2.1]heptane or bicyclo[2.2.2]octane.

The term "—(C$_3$-C$_6$)-cycloalkyl" or "—(C$_3$-C$_8$)-cycloalkyl" is understood as meaning radicals which are derived from monocycles having 3 to 6 or 3 to 8 carbon atoms in the ring such as cyclopropane, cyclobutane, cyclopentane, cyclohexane, cyclo-heptane or cyclooctane.

The term "—(C$_6$-C$_{14}$)-aryl" is understood as meaning aromatic hydrocarbon radicals having 6 to 14 carbon atoms in the ring. —(C$_6$-C$_{14}$)-Aryl radicals are, for example, phenyl, naphthyl, for example 1-naphthyl, 2-naphthyl, anthryl or fluorenyl. Naphthyl radicals and in particular phenyl radicals are preferred aryl radicals.

The term "four- to fifteen-membered Het" or "Het" is understood as meaning ring systems having 4 to 15 carbon atoms, which are present in one, two or three ring systems connected to one another and in which one, two, three or four identical or different heteroatoms from the group consisting of oxygen, nitrogen or sulfur can replace the respective carbon atoms. Examples of these ring systems are the radicals acridinyl, azepinyl, azetidinyl, benzimidazolinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, beta-carbolinyl, quinazolinyl, quinolinyl, quinolizinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl or xanthenyl.

The term "—(C$_1$-C$_3$)-fluoroalkyl" is understood as meaning a partially or completely fluorinated alkyl radical which is derived, for example, from the following radicals —CF$_3$, —CHF$_2$, —CH$_2$F, —CHF—CF$_3$, —CHF—CHF$_2$, —CHF—CH$_2$F, —CH$_2$—CF$_3$, —CH$_2$—CHF$_2$, —CH$_2$—CH$_2$F, —CF$_2$—CF$_3$, —CF$_2$—CHF$_2$, —CF$_2$—CH$_2$F, —CH$_2$—CHF—CF$_3$, —CH$_2$—CHF—CHF$_2$, —CH$_2$—CHF—CH$_2$F, —CH$_2$—CH$_2$—CF$_3$, —CH$_2$—CH$_2$—CHF$_2$, —CH$_2$—CH$_2$—CH$_2$F, —CH$_2$—CF$_2$—CF$_3$, —CH$_2$—CF$_2$—CHF$_2$, —CH$_2$—CF$_2$—CH$_2$F, —CHF—CHF—CF$_3$, —CHF—CHF—CHF$_2$, —CHF—CHF—CH$_2$F, —CHF—CH$_2$—CF$_3$, —CHF—CH$_2$—CHF$_2$, —CHF—CH$_2$—CH$_2$F, —CHF—CF$_2$—CF$_3$, —CHF—CF$_2$—CHF$_2$, —CHF—CF$_2$—CH$_2$F, —CF$_2$—CHF—CF$_3$, —CF$_2$—CHF—CHF$_2$, —CF$_2$—CHF—CH$_2$F, —CF$_2$—CH$_2$—CF$_3$, —CF$_2$—CH$_2$—CHF$_2$, —CF$_2$—CH$_2$—CH$_2$F, —CF$_2$—CF$_2$—CF$_3$, —CF$_2$—CF$_2$—CHF$_2$ or —CF$_2$—CF$_2$—CH$_2$F.

The term "halogen" is understood as meaning fluorine, chlorine, bromine or iodine; fluorine, chlorine or bromine is preferred, in particular chlorine or bromine.

The term "a basic nitrogen-containing group" is understood as meaning radicals where the conjugated acid of this group has a pKa of approximately 5 to 15.

Examples of this basic nitrogen-containing group are amino, aminomethylene, amidino (carbamimidoyl), guanidino, azetidinyl, pyrrolidinyl, piperidinyl, pyridinyl or aminopyridinyl.

Functional groups of the intermediates used, for example amino or carboxyl groups, can be masked here by suitable protective groups. Suitable protective groups for amino functions are, for example, the t-butoxycarbonyl, the benzyloxycarbonyl or the phthaloyl group, and the trityl or tosyl protective group. Suitable protective groups for the carboxyl function are, for example, alkyl, aryl or arylalkyl esters. Protective groups can be introduced and removed by techniques which are well-known or described here (see Green, T. W., Wutz, P. G. M., *Protective Groups in Organic Synthesis* (1991), 2nd Ed., pp. 1-16, Wiley-Interscience, or Kocienski, P., *Protecting Groups* (1994), Thieme). The term protective group can also include polymer-bound protective groups. Such masked compounds according to formula (I), in which, for example, the functional groups of the radicals R1, R2, R3, R4, R5 or R6 can optionally also be masked, can, although optionally themselves not pharmacologically active, optionally be converted after administration to mammals by metabolization to the pharmacologically active compounds according to the invention.

The compounds according to the invention can be prepared by well-known processes or according to processes described here.

The invention furthermore relates to a process for the preparation of the compound of the formula I and/or of a stereoisomeric form of the compound of the formula I and/or of a physiologically tolerable salt of the compound of the formula I, which comprises preparing the compound of the formula I according to Scheme 1.

Scheme 1:

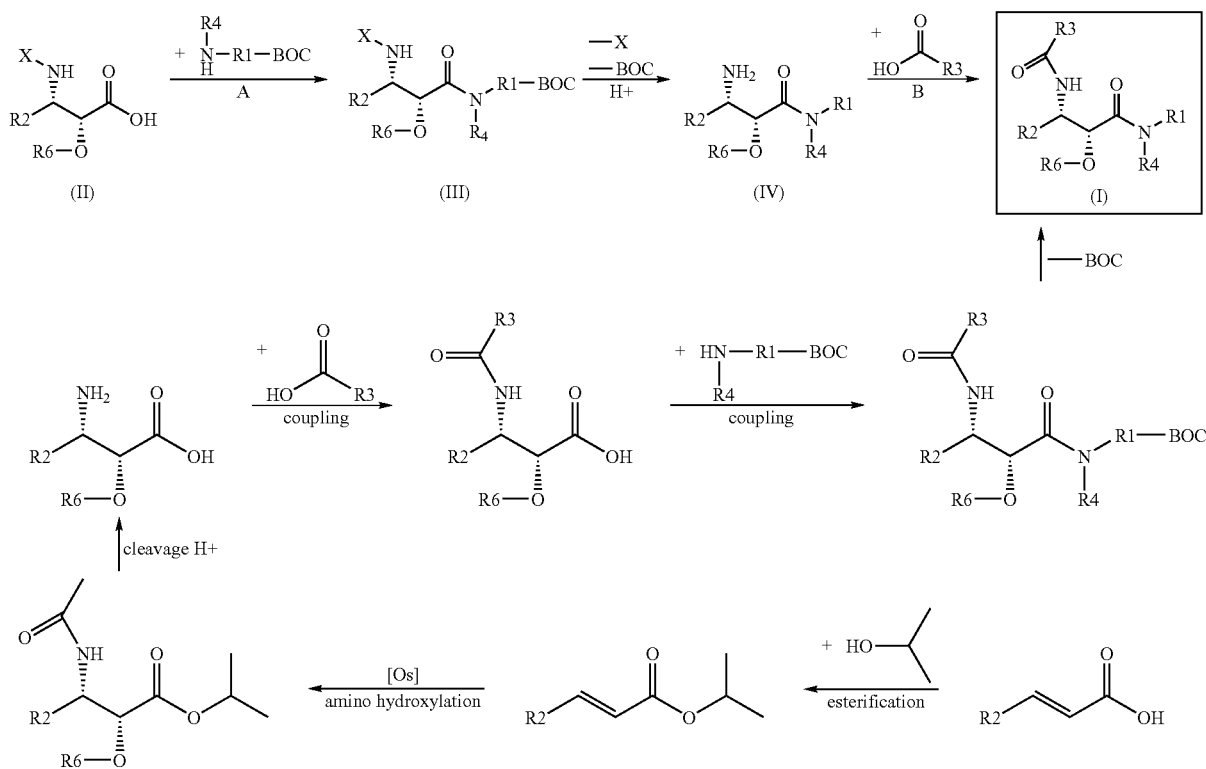

The radicals R1, R2, R3 and R4 used in Scheme 1 have the same meaning as those in the compound of the formula I, X is an amino protective group, BOC is the protective group butoxycarbonyl and Os is osmium.

In a process step A, the compound of the formula II, for example (2R,3S)-3-(Boc-amino)-2-hydroxy-3-phenylpropanoic acid, is dissolved in a solvent such as dimethylformamide (DMF), dichloromethane ($CH_2Cl_2$), tetrahydrofuran (THF), N-methylpyrrolidinone (NMP) or dioxane and reacted with a suitable amine of the formula NH(R1-BOC)—R4, for example 6- or 7-aminoisoquinolin-1-yl)-N-di-carboxyamino tert-butyl ester, 2-amino-6-nitrobenzothiazole or tertiary butyl 2,5-diaminobenzimidazole-1-carboxylate to give the corresponding amide (III). For this, as described above, a customary coupling reagent such as TOTU, PyBrop, PyBop, HATU or EDC and a suitable base such as amine bases such as diisopropylethylamine (Hünig's Base), triethylamine ($NEt_3$) or 4-dimethylamino-pyridine (4-DMAP) are used.

Subsequently, compound IV is obtained by removal of the protective groups such as t-butyloxycarbonyl (BOC) according to standard methods (such as with TFA-$CH_2Cl_2$). (For alternative methods for the removal of protective groups see z. B. Kocienski, P. J., *Protecting groups*, Thieme Verlag 1994).

By fresh amide coupling with suitable carboxylic acids of the type R3-COOH under analogous conditions as described in process A, the desired compound of type I is finally obtained.

In the case of compounds of type II which are not obtainable, for example R2=Het, compounds of type I can also be prepared via a route (for R6=H) starting from the corresponding cinnamic acids. Here, in a first step, reaction of the cinnamic acids to give the corresponding isopropyl cinnamates takes place followed by an aminohydroxylation according to published standard processes. After subsequent acidic acetyl removal, two-fold amide coupling (1. with R3-COOH and 2. with NH(R1)-R2) and removal of BOC analogously to the conditions described above, the desired compounds of the type I are likewise obtained. For both processes described, the compounds (I) where R=H can in principle be converted by means of methods known from the literature (for example ester formation or carbamoylation) directly to the derivatives where R6 is not equal to H.

The invention further relates to a process for the preparation of the compound of the formula I and/or of a stereoisomeric form of the compound of the formula I and/or of a physiologically tolerable salt of the compound of the formula I, which comprises a) reacting a compound of the formula II

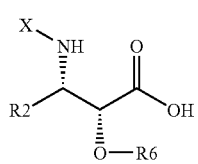

(II)

where X is an amino protective group and the radicals R2 and R6 are as defined in formula I with a compound NH(R1)(R4) to give a compound of the formula III,

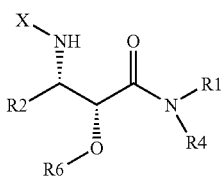

where X is an amino protective group and the radicals R1, R2, R4 and R6 are as defined in formula I and converting the compound of the formula III to a compound of the formula IV by removal of the protective group,

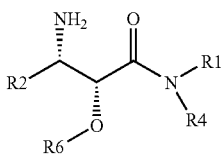

where the radicals R1, R2, R4 and R6 are as defined in the formula I, and reacting with the compound of the formula V

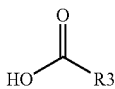

to give the compound of the formula I, or b) either isolating the compound of the formula I prepared according to process a) in free form or releasing it from physiologically intolerable salts or, in the case of the presence of acidic or basic groups, converting it to physiologically tolerable salts, or c) separating a compound of the formula I prepared according to process a), or a suitable precursor of the formula I, which on account of its chemical structure occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

A compound of the formula I prepared according to Scheme 1, or a suitable precursor of the formula I which on account of its chemical structure occurs in enantiomeric forms, can be separated into the pure enantiomers (process c) by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups, or the compound of the formula I prepared according to Scheme 1 can either be isolated in free form or, in the case of the presence of acidic or basic groups, converted to physiologically tolerable salts (process b).

In process step c), the compound of the formula I, if it occurs as a mixture of diastereomers or enantiomers or is obtained in the chosen synthesis as mixtures thereof, is separated into the pure stereoisomers, either by chromatography on an optionally chiral support material, or, if the racemic compound of the formula I is capable of salt formation, by fractional crystallization of the diastereomeric salts formed using an optically active base or acid as an auxiliary. Suitable chiral stationary phases for the thin-layer or column-chromatographic separation of enantiomers are, for example, modified silica gel supports ("Pirkle phases") and high molecular weight carbohydrates such as triacetylcellulose. For analytical purposes, gas chromatographic methods on chiral stationary phases can also be used after appropriate derivatization known to the person skilled in the art. For the separation of the enantiomers of the racemic carboxylic acids, the diastereomeric salts of differing solubility are formed using an optically active, usually commercially obtainable, base such as (−)-nicotine, (+)- and (−)-phenylethylamine, quinine bases, L-lysine or L- and D-arginine, the more poorly soluble component is isolated as a solid, the more readily soluble diastereomer is precipitated from the mother liquor and the pure enantiomers are obtained from the diastereomeric salts thus obtained. In a manner which is identical in principle, the racemic compounds of the formula I, which contain a basic group such as an amino group, can be converted into the pure enantiomers using optically active acids, such as (+)-camphor-10-sulfonic acid, D- and L-tartaric acid, D- and L-lactic acid and (+) and (−)-mandelic acid. Chiral compounds which contain alcohol or amine functions can also be converted using appropriately activated or optionally N-protected enantiomerically pure amino acids to the corresponding esters or amides, or conversely chiral carboxylic acids can be converted using carboxy-protected enantiomerically pure amino acids to the amides or, using enantiomerically pure hydroxycarboxylic acids such as lactic acid, to the corresponding chiral esters. Then, the chirality of the amino acid or alcohol radical introduced in enantiomerically pure form can be used for the separation of the isomers, by carrying out a separation of the diastereomers now present by crystallization or chromatography on suitable stationary phases and then removing the entrained chiral moiety again by means of suitable methods.

Furthermore, in the case of some of the compounds according to the invention the possibility arises of employing diastereomerically or enantiomerically pure starting products for the preparation of the backbone structures. By this means, other or simplified processes can be employed for the purification of the final products. These starting products were prepared beforehand in enantiomerically or diastereomerically pure form according to processes known from the literature. This can mean, in particular, that in the synthesis of the skeletal structures either enantioselective processes are used, or else an enantiomeric (or diastereomeric) separation is carried out at an earlier stage of the synthesis and not only at the stage of the final products. Likewise, a simplification of the separations can be achieved by proceeding in two or more stages.

Acidic or basic products of the compound of the formula I can be present in the form of their salts or in free form. Pharmacologically tolerable salts are preferred, for example alkali metal or alkaline earth metal salts such as hydrochlorides, hydrobromides, sulfates, hemisulfates, all possible phosphates, and salts of the amino acids, natural bases or carboxylic acids.

The preparation of physiologically tolerable salts from compounds of the formula I capable of salt formation, including their stereoisomeric forms, according to process step c) is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the formula I form stable alkali metal, alkaline earth metal or optionally substituted ammonium salts.

If the compounds of the formula I have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments which contain an efficacious amount of at least one compound of the formula I and/or of a physiologically tolerable salt of the compound of the formula I and/or an optionally stereoisomeric form of the compound of the formula I, together with a pharmaceutically suitable and physiologically tolerable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the formula I can be employed in patients who are suffering from disorders of well-being or diseases which accompany thromboses, embolisms, hypercoagulability or fibrotic changes.

These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar events such as stent implantations and bypass operations. Furthermore, the compounds of the formula I can be employed in all events which lead to contact of the blood with foreign surfaces, as in dialysis patients and patients with indwelling catheters. Compounds of the formula I can also be employed in order to reduce the risk of thrombosis after surgical interventions, such as in knee and hip joint operations.

Compounds of the formula I are suitable for the treatment of patients with disseminated intravascular coagulation, sepsis and other intravascular events which accompany inflammation. Furthermore, compounds of the formula I are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the formula I are suitable for the retardation or prevention of such processes.

Further indications for the use of the compounds of the formula I are fibrotic changes of the lungs such as chronic obstructive pulmonary disease, adult respiratory distress syndrome (ARDS) and of the eye, such as fibrin deposits after eye operations. Compounds of the formula I are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for the production of a medicament, which comprises bringing at least one compound of the formula I into a suitable administration form using a pharmaceutically suitable and physiologically tolerable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the formula I according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to formula I, daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the formula I can be administered both as a monotherapy and in combination or together with all antithrombotics (anticoagulants and platelet aggregation inhibitors), thrombolytics (plasminogen activators of any type), other profibrinolytically active substances, hypotensives, blood sugar regulators, lipid-lowering agents and antiarrhythmics.

EXAMPLES

Final products are usually determined by mass spectroscopic methods (FAB, ESI-MS) and $^1$H-NMR, in each case the main peak or the two main peaks are indicated. Temperature data in degrees Celsius, yld. is yield. Abbreviations used are either explained or correspond to the customary conventions. If not stated otherwise, chromatographic separations were carried out on silica gel using ethyl acetate/heptane mixtures as eluents. Preparative separations on reversed phase (RP) silica gel (HPLC) were carried out, if not stated otherwise, under the following conditions: column Merck Hibar RT 250-25 LiChrospher 100 RP-18e 5 μm, Merck KGaA, Germany, Life Science & Analytics, 64293 Darmstadt; mobile phase A: H₂O+0.1% TFA, phase B: 80% acetonitrile+0.1% TFA, flow 25 ml/min., 0 to 7 min. 100% A, 7 to 22 min. to 100% B, 22 to 30 min. 100% B, 30 to 33 min. to 100% A, 33 to 35 min. 100% A. The evaporation of solvents was usually carried out under reduced pressure at 35° C. to 45° C. on a rotary evaporator. If not mentioned otherwise, the LC/MS analyses were carried out under the following conditions:

| Method A: | |
|---|---|
| Column: | YMC J'shere H80 33 × 2.1 mm; Waters GmbH, Helfmann-Park 10, 65760 Eschborn, Germany; packing material 4 μm, |
| Solvent: | ACN + 0.05% TFA:H₂O + 0.05% TFA (flow 1.3 ml/min) |
| Gradient: | 5:95 (0 min) to 95:5 (2.5 min) to 95:5 (3.0 min) |
| Ionization: | ESI⁺ |
| Method B: | |
| Column: | YMC J'shere H80 33 × 2.1 mm; packing material 4 μm, |
| Solvent: | ACN + 0.05% TFA:H₂O + 0.05% TFA (flow 1 ml/min) |
| Gradient: | 5:95 (0 min) to 95:5 (3.4 min) to 95:5 (4.4 min) |
| Ionization: | ESI⁺ |
| Method C: | |
| Column: | YMC J'shere H80 33 × 2.1 mm 4 μm, |
| Solvent: | ACN + 0.08% TFA:H₂O + 0.1% TFA (flow 1.3 ml/min) |
| Gradient: | 5:95 (0 min) to 95:5 (2.5 min) to 95:5 (3 min) |
| Ionization: | ESI⁺ |
| Method D: | |
| Column: | YMC J'shere ODS H80 20 × 2.1 mm packing material 4 μm, |
| Solvent: | ACN:H₂O + 0.05% TFA (flow 1 ml/min) |
| Gradient: | 4:96 (0 min) to 95:5 (2 min) to 95:5 (2.4 min) to 96:4 (2.45 min) |
| Ionization: | ESI⁺ |

Preparative HPLC was carried out using the following method:

| | |
|---|---|
| Column: | Waters Atlantis dC18 OBD 30 × 100 mm 5 μm; Waters GmbH, Helfmann-Park 10, 65760 Eschborn, Germany |
| Solvent: | ACN:H₂O + 0.1% TFA (flow 60 ml/min) |
| Gradient: | 10:90 (0 min) to 90:10 (10 min) |

Abbreviations Used:
ACN acetonitrile
Boc butoxycarbonyl
DCM dichloromethane
(DHQ)₂PHAL 1-[(R)-((4S,5R)-5-ethyl-1-azabicyclo[2.2.2]oct-2-yl)-(6-methoxyquinolin-4-yl)methoxy]-4-[(R)-((4R,5S)-5-ethyl-1-azabicyclo-[2.2.2]oct-2-yl)-(6-methoxyquinolin-4-yl)methoxy]phthalazine
DIPEA N,N-diisopropylethylamine (Hünig's base)
DMF dimethylformamide
DMSO dimethyl sulfoxide
EDC N'-(3-dimethylaminopropyl)-N-ethylcarbodiimide
HATU O-(7-azabenzotriazol-1-yl)-N,N,N',N'-tetramethyluronium hexafluorophosphate
HOAt 1-hydroxy-7-azabenzotriazole
K₂[OsO₂(OH)₄] potassium osmate dihydrate
LC/MS liquid chromatography-mass spectroscopy
MeOH methanol
NMM N-methylmorpholine
PyBop 1-benzotriazolyloxytripyrrolidinophosphonium hexafluorophosphate
PyBrop bromotrispyrrolidinephosphonium hexafluorophosphate
R$_t$ retention time
TFA trifluoroacetic acid
TOTU O-((ethoxycarbonyl)cyanomethylenimino)-N,N,N',N'-tetramethyluronium tetrafluoroborate
RT room temperature (21° C. to 24° C.)

Example 1

N-[(1S,2R)-2-(1-Aminoisoquinolin-7-ylcarbamoyl)-2-hydroxy-1-phenylethyl]-4-tert-butylbenzamide; compound with trifluoroacetic acid

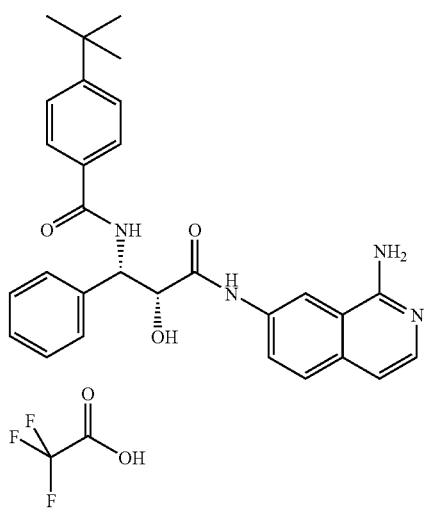

Process Step 1

[7-((2R,3S)-3-tert-Butoxycarbonylamino-2-hydroxy-3-phenylpropionylamino)-isoquinolin-1-yl]-N-dicarboxyamino tert-butyl ester

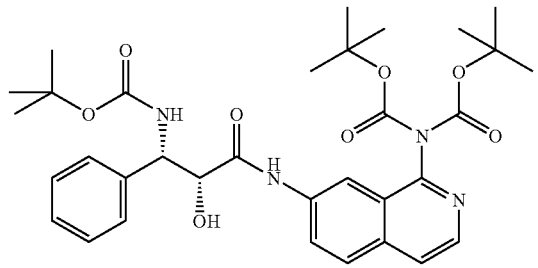

0.69 ml (6.26 mmol) of NMM was added to a solution of 0.75 g (2.08 mmol) of 7-aminoisoquinolin-1-yl-N-dicarboxyamino tert-butyl ester, (2R,3S)-3-(Boc-amino)-2-hydroxy-3-phenylpropanoic acid (0.587 g, 2.08 mmol) and HOAt (0.284 g, 2.08 mmol) in 10 ml of DMF with stirring for 10 minutes (min). After the addition of 0.973 g of PyBrop (2.08 mmol), the mixture was stirred at RT for 18 hours (h). Subsequently, water was added to the reaction mixture, and it was extracted with ethyl acetate, dried using sodium sulfate, filtered and concentrated under reduced pressure and the residue was purified using silica gel chromatography (ethyl acetate:n-heptane 1:2).

0.56 g (yield: 43%) of the purified title compound was obtained.

LC/MS (Method D) (M+H-BOC)+ 523

7-Aminoisoquinolin-1-yl-N-dicarboxyamino tert-butyl ester was obtained as in the process described in WO 00/71507, page 92.

Process Step 2

(2R,3S)-3-Amino-N-(1-aminoisoquinolin-7-yl)-2-hydroxy-3-phenylpropionamide; compound with trifluoroacetic acid

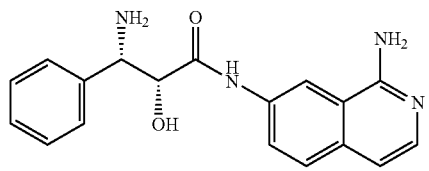

3 ml of TFA were added to 0.56 g (0.89 mmol) of the compound from Process step 1 in DCM (9 ml). Subsequently, the reaction mixture was stirred at RT for 3 h. The solvents were distilled off under reduced pressure and the solid was taken up in MeOH and water and finally lyophilized. 0.485 g (yield: 99%) of the purified title compound was obtained as a white solid. LC/MS (Method D) (M+H)+ 323

Process Step 3

N-[(1S,2R)-2-(1-Aminoisoquinolin-7-ylcarbamoyl)-2-hydroxy-1-phenylethyl]-4-tert-butylbenzamide; compound with trifluoroacetic acid 0.038 ml (0.22 mmol) of DIPEA was added to a solution of 40 mg (0.073 mmol) of the compound from Process step 2,4-tertiary-butylbenzoic acid (12.9 mg, 0.073 mmol), HOAt (9.89 mg, 0.073 mmol) and HATU (27.6 mg, 0.073 mmol) in DMF (1.5 ml). Subsequently, the reaction mixture was stirred for 42 h at RT. The reaction mixture was filtered and purified by means of preparative high pressure liquid chromatography (HPLC). The purified fractions of the product were lyophilized and a white solid was obtained. Yield 53%

LCMS (Method A) 482.23 ($R_t$=1.43 min, 100%)

$^1$H NMR (500 MHz, DMSO-$d_6$) δ (ppm): 1.28 (s, 9H), 4.54 (t, 1H), 5.56 (dd, 1H), 6.31 (d, 1H), 7.18 (d, 1H), 7.25 (t, 1H), 7.33 (t, 2H), 7.47 (d, 4H), 7.58 (d, 1H), 7.78 (d, 2H), 7.91 (d, 1H), 8.01 (dd, 1H), 8.45 (d, 1H), 8.74 (s, 1H), 8.91 (s, 2H), 10.36 (s, 1H), 12.90 (s, 1H)

Example 2

N-[(1S,2R)-2-(1-Aminoisoquinolin-6-ylcarbamoyl)-2-hydroxy-1-phenylethyl]-4-diethylaminobenzamide; compound with HCl

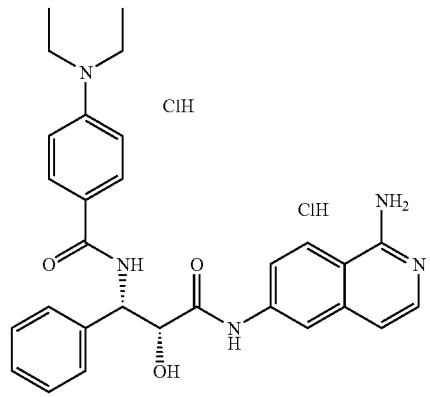

Process Step 1

[6-((2R,3S)-3-tert-Butoxycarbonylamino-2-hydroxy-3-phenylpropionylamino)-isoquinolin-1-yl]-N-dicarboxyamino tert-butyl ester 6-Aminoisoquinolin-1-yl-N-dicarboxyamino tert-butyl ester (1.5 g, 4.17 mmol) was reacted analogously to the preparation of Example 1, Process step 1. 0.82 g of the title compound was obtained; yield: 32% of a solid.

LC/MS (Method D) (M+H)+ 623

6-Aminoisoquinolin-1-yl-N-dicarboxyamino tert-butyl ester was obtained as in the process described in WO2004/072101, page 108.

Process Step 2

(2R,3S)-3-Amino-N-(1-aminoisoquinolin-6-yl)-2-hydroxy-3-phenylpropionamide; compound with trifluoroacetic acid The compound from Process step 1 (0.82 g, 1.32 mmol) was reacted analogously to the preparation of Example 1, Process step 2. 0.71 g of the title compound (yield: 98%) was obtained as a solid.

LC/MS (Method D) (M+H)+ 323

Process Step 3

N-[(1S,2R)-2-(1-Aminoisoquinolin-6-ylcarbamoyl)-2-hydroxy-1-phenylethyl]-4-diethylaminobenzamide; compound with hydrochloric acid The product obtained from Process step 2 (0.6 g, 1.09 mmol), 4-diethylaminobenzoic acid (0.21 g, 1.09 mmol), HOAt (148 mg, 1.09 mmol) and HATU (415 mg, 1.09 mmol) were dissolved in 10 ml of DMF and 0.56 ml of DIPEA (3.27 mmol) was added. Subsequently, the reaction mixture was stirred at RT for 18 h. The reaction mixture was filtered and purified by means of preparative HPLC. The purified fractions of the product were lyophilized, dissolved in 2 ml of MeOH and subsequently treated with 5 ml of 5 M HCl and lyophilized again. 278 mg of a white solid were obtained. Yield: 45%

LC/MS (Method B) 497.24 ($R_t$=1.15 min, 100%)

$^1$H NMR (500 MHz, DMSO-$d_6$) δ (ppm): 1.08 (t, 6H), 3.38 (d, 4H), 4.56 (d, 1H), 5.54 (dd, 1H), 6.65 (s, 2H), 7.14 (d, 1H), 7.24 (t, 1H), 7.32 (t, 2H), 7.45 (d, 2H), 7.59 (t, 1H), 7.71 (s, 2H), 7.91 (dd, 1H), 8.15 (s, 1H), 8.29 (d, 1H), 8.49 (d, 1H), 8.90 (s, 2H), 10.64 (s, 1H), 12.90 (s, 1H)

Example 3

N-[(1S,2R)-2-(2-Aminobenzothiazol-6-ylcarbamoyl)-2-hydroxy-1-phenylethyl]-4-isopropylbenzamide; compound with trifluoroacetic acid

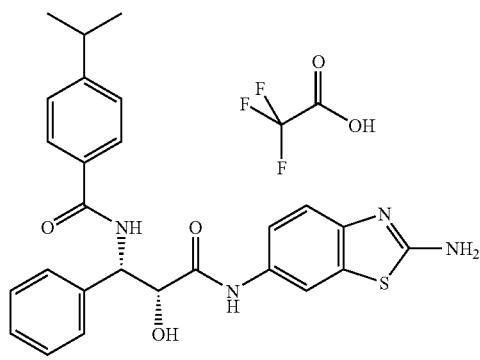

Process Step 1

Benzothiazole-2,6-diamine

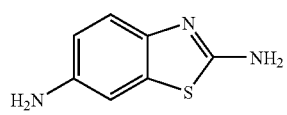

2-Amino-6-nitrobenzothiazole (1.0 g, 5.12 mmol) was dissolved in 100 ml of MeOH and palladium on activated carbon (10%, 545 mg, 0.51 mmol) was added. The reaction mixture was hydrogenated using hydrogen at RT (3 bar $H_2$) for 2.5 h. The mixture was filtered, the solvent was removed under reduced pressure and the residue was purified using silica gel chromatography (ethyl acetate:n-heptane 1:2). 0.81 g (yield: 96%) of the purified title compound was obtained.

LC/MS (Method D) (M+H)$^+$ 166

Process Step 2

[(1S,2R)-2-(2-Aminobenzothiazol-6-ylcarbamoyl)-2-hydroxy-1-phenylethyl]-carboxyamino tert-butyl ester The compound obtained from Process step 1 (71 mg, 0.43 mmol) was reacted analogously to the preparation of Example 1, Process step 1.180 mg of the title compound were obtained; yield: 98% of a solid. LC/MS (Method D) (M+H)$^+$ 429

Process Step 3

(2R,3S)-3-Amino-N-(2-aminobenzothiazol-6-yl)-2-hydroxy-3-phenylpropionamide; compound with trifluoroacetic acid The compound from Process step 2 (180 mg, 0.42 mmol) was reacted analogously to the preparation of Example 1, Process step 2.177 mg of the title compound were obtained; yield: 76% of a solid. LC/MS (Method D) (M+H)$^+$ 329

Process Step 4

N-[(1S,2R)-2-(2-Aminobenzothiazol-6-ylcarbamoyl)-2-hydroxy-1-phenyl-ethyl]-4-isopropylbenzamide; compound with trifluoroacetic acid The product obtained from Process step 3 (78 mg, 0.14 mmol), 4-isopropylbenzoic acid (23 mg, 0.14 mmol), HOAt (19 mg, 0.14 mmol) and HATU (53 mg, 0.14 mmol) were dissolved in 2 ml of DMF and 0.046 ml of NMM (0.42 mmol) was added. Subsequently, the reaction mixture was stirred at RT for 18 h. The reaction mixture was filtered and purified by means of preparative HPLC. The purified fractions of the product were lyophilized. 33 mg of a white solid were obtained. Yield: 40%

LC/MS (Method A) 474.17 ($R_t$=1.63 min, 100%)

$^1$H NMR (500 MHz, DMSO-$d_6$) δ (ppm): 1.20 (d, 6H), 2.94 (h, 1H), 4.44 (d, 1H), 5.49 (dd, 1H), 7.24 (t, 1H), 7.28-7.34 (m, 5H), 7.38 (dd, 1H), 7.44 (d, 2H), 7.77 (d, 2H), 8.05 (d, 1H), 8.15 (s, 1H), 8.43 (d, 1H), 9.95 (s, 1H)

Example 4

N-[(1R,2R)-2-(1-Aminoisoquinolin-6-ylcarbamoyl)-1-furan-2-yl-2-hydroxyethyl]-4-diethylaminobenzamide; compound with trifluoroacetic acid

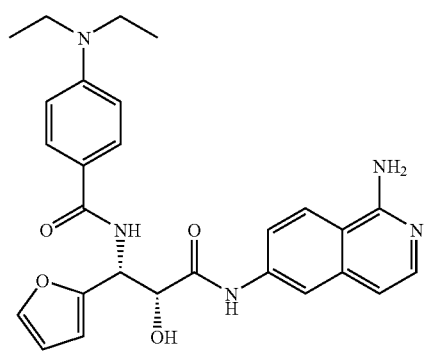

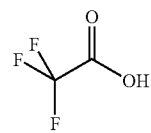

Process Step 1

Isopropyl (E)-3-furan-2-ylacrylate

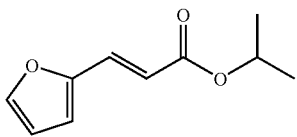

1.46 ml of thionyl chloride (20 mmol) were added to a solution of 1.38 g of 3-(2-furyl)acrylic acid (10 mmol) in 10 ml of chloroform and 0.1 ml of DMF. The solution was warmed to 70° C. and kept at this temperature for 1 h, then the solvents were removed under reduced pressure and the residue was dissolved in 6.6 ml of DCM and 3.3 ml of pyridine and subsequently cooled to 0° C. 0.96 ml of 2-propanol (12.5 mmol) was added, the temperature was increased to RT and the reaction mixture was stirred for 2.5 h. It was acidified with 30 ml of 1 M hydrochloric acid and extracted with 150 ml of ethyl acetate. The organic phase was washed with aqueous sodium hydrogencarbonate solution, dried over sodium sulfate, filtered and the solvents were removed under reduced pressure. 1.72 g (yield: 96%) of the title compound were obtained. LC/MS (Method D) (M+H-isopropyl)+ 139

Process Step 2

Isopropyl (2R,3R)-3-acetylamino-3-furan-2-yl-2-hydroxypropionate

The reaction was carried out as described in Sharpless et. al. Angew. Int. Ed. 1997, 36, 1483.

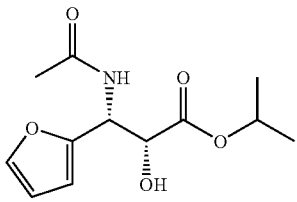

14 ml of tertiary-butanol and 117 mg of (DHQ)$_2$PHAL (0.15 mmol) were added to a solution containing 128 mg of lithium hydroxide monohydrate (3.06 mmol) and 44.5 mg of K$_2$[OsO$_2$ (OH)$_4$] (0.12 mmol) in 7 ml of water and the solution was stirred at RT for 10 min. After the addition of 14 ml of water, the mixture was cooled to 4° C. and 0.54 g (3 mmol) of the compound according to Process step 1 and 455 mg of N-bromoacetamide (3.3 mmol) were added. The mixture was stirred at 4° C. for 3.5 h. Then 1.2 g of sodium sulfite were added and the mixture was stirred for 30 min at RT. Water was added and the aqueous phase was extracted with ethyl acetate. The organic phase was dried using sodium sulfate, filtered, the solvent was removed under reduced pressure and the residue was purified using silica gel chromatography (ethyl acetate:n-heptane 2:3). 112 mg (yield: 15%) of the purified title compound were obtained.

LC/MS (Method D) (M+H)+ 256

Process Step 3

(2R,3R)-3-Amino-3-furan-2-yl-2-hydroxypropionic acid; compound with hydrochloric acid

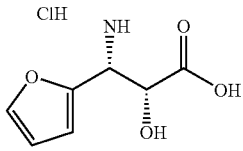

112 mg of the compound obtained from Process step 2 (0.44 mmol) were dissolved in 8 ml of hydrochloric acid (10%) and heated at 110° C. for 3 h. Water was added to the reaction mixture and, after lyophilization, 91 mg (yield 100%) of the pure title compound was obtained.

LC/MS (Method D) (M+H—NH$_2$)+ 155

Process Step 4

(2R,3R)-3-(4-Diethylaminobenzoylamino)-3-furan-2-yl-2-hydroxypropionic acid

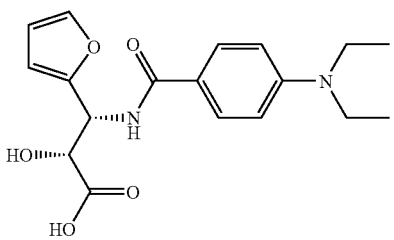

89 mg of 4-diethylaminobenzoic acid (0.46 mmol) and 152 mg of TOTU (0.46 mmol) were dissolved in 2 ml of DMF and 255 µl of NMM (2.31 mmol) were added. The reaction mixture was stirred at RT for 30 min and 96 mg of the product from Process step 3 (0.46 mmol) were added. Subsequently, the reaction mixture was stirred for 18 h at RT. The mixture was filtered and purified by means of preparative HPLC. The purified fractions of the products were lyophilized. 142 mg of a white solid were obtained. Yield: 89%

LC/MS (Method D) (M+H)+ 347

Process Step 5

{6-[(2R,3R)-3-(4-Diethylaminobenzoylamino)-3-furan-2-yl-2-hydroxy-propionylamino]isoquinolin-1-yl}-N-dicarboxyamino tert-butyl ester

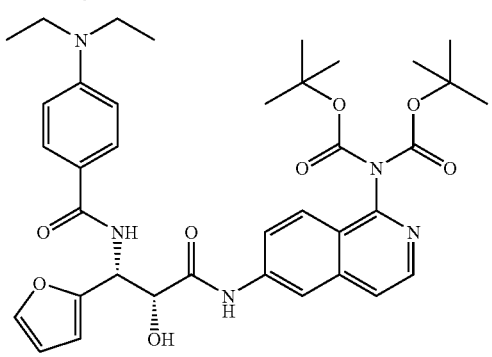

48.2 mg of the product obtained in Process step 4 (0.14 mmol), 50 mg of 7-aminoisoquinolin-1-yl)-N-dicarboxyamino tert-butyl ester (0.14 mmol), 19 mg of HOAt (0.14 mmol) and 64.8 mg of PyBrop (0.14 mmol) were dissolved in 1.5 ml of DMF and 61.3 µl of NMM (0.56 mmol) were subsequently added and the reaction mixture was then stirred at RT for 42 h. The mixture was filtered and purified by means of preparative HPLC. The purified fractions of the product were lyophilized. The lyophilized solid was then dissolved and purified using silica gel chromatography (DCM:MeOH 30:1). 13 mg (yield: 14%) of the purified title compound were obtained.

LC/MS (Method D) (M+H)+ 688

Process Step 6

N-[(1R,2R)-2-(1-Aminoisoquinolin-6-ylcarbamoyl)-1-furan-2-yl-2-hydroxyethyl]-4-diethylaminobenzamide; compound with trifluoroacetic acid The product obtained from Process step 5 (13 mg, 18.9 µmol) was dissolved in 3 ml of DCM and 1 ml of TFA was added. The reaction mixture was then stirred for 1 h at RT. The reaction mixture was filtered and the solvents were removed under reduced pressure. The residue was dissolved in MeOH and water, lyophilized and 11 mg of a white solid were obtained. Yield: 97%. LC/MS (Method A) 487.22 ($R_t$=1.00 min, 100%)

$^1$H NMR (500 MHz, DMSO-$d_6$) δ (ppm): 1.08 (t, 6H), 3.37 (q, 4H), 4.64 (d, 1H), 5.65 (dd, 1H), 6.32 (d, 1H), 6.40 (d, 1H), 6.63 (d, 2H), 7.15 (d, 1H), 7.59 (m, 2H), 7.67 (d, 2H), 7.91 (dd, 1H), 7.96 (d, 1H); 8.31 (d, 1H), 8.45 (d, 1H), 8.81 (s, 2H), 10.56 (s, 1H), 12.73 (s, 1H)

Example 5

N-[(1S,2R)-2-(2-Aminobenzothiazol-6-ylcarbamoyl)-1-(2-chlorophenyl)-2-hydroxyethyl]-4-isopropylbenzamide; compound with trifluoroacetic acid

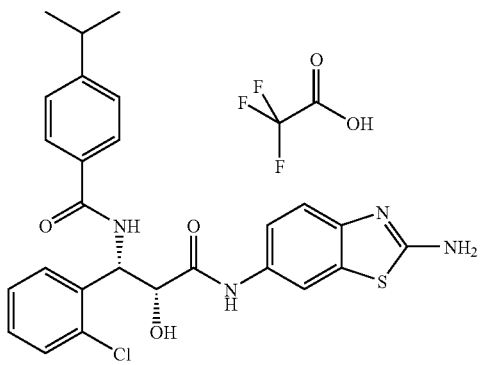

Process Step 1

Isopropyl (E)-3-(2-chlorophenyl)acrylate 1.83 g of 2-chlorocinnamic acid (10 mmol) were reacted analogously to the preparation of Example 4, Process step 1.1.92 g of the title compound were obtained; yield: 86%. LC/MS (Method D) (M+H)+ 225

Process Step 2

Isopropyl (2R,3S)-3-acetylamino-3-(2-chlorophenyl)-2-hydroxypropionate 1.9 g of the compound obtained from Process step 1 (8.46 mmol) were reacted analogously to the preparation of Example 4, Process step 2.1.93 g of the title compound were obtained; yield: 76%.

LC/MS (Method D) (M+H)+ 300

Process Step 3

(2R,3S)-3-Amino-3-(2-chlorophenyl)-2-hydroxypropionic acid; compound with hydrochloric acid 1.93 g of the compound obtained from Process step 2 (6.44 mmol) were reacted analogously to the preparation of Example 4, Process step 3.1.6 g of the title compound were obtained; yield: 99%.

LC/MS (Method D) (M+H)+ 216

Process Step 4

(2R,3S)-3-(2-Chlorophenyl)-2-hydroxy-3-(4-isopropylbenzoylamino)propionic acid 525 mg of 4-isopropylbenzoic acid (3.2 mmol) and 525 mg of the process product from step 3 (3.2 mmol) were reacted analogously to Example 4, Process step 4.

630 mg of the title compound were obtained as a white solid; yield: 54%. LC/MS (Method D) (M+H)+ 362

Process Step 5

N-[(1S,2R)-2-(2-Aminobenzothiazol-6-ylcarbamoyl)-1-(2-chlorophenyl)-2-hydroxyethyl]-4-isopropylbenzamide; compound with trifluoroacetic acid 77 mg of the compound obtained from Process step 4 (0.21 mmol) were reacted with 35 mg of the compound obtained from Example 3, Process step 1 (0.21 mmol) analogously to the preparation of Example 4, Process step 5. 87 mg of the title compound were obtained; yield: 66%.

LC/MS (Method A) 508.13 ($R_t$=1.40 min, 100%)

$^1$H NMR (400 MHz, DMSO-$d_6$) δ (ppm): 1.19 (d, 6H), 2.92 (h, 1H), 4.41 (d, 1H), 5.89 (dd, 1H), 6.42 (s, 1H), 7.27-7.34 (m, 5H), 7.45 (m, 2H), 7.56 (dd, 1H), 7.76 (d, 2H), 8.07 (s, 1H), 8.10 (d, 1H), 8.39 (d, 1H), 9.85 (s, 1H)

Example 6

N-[(1S,2R)-2-(2-Amino-3H-benzimidazol-5-ylcarbamoyl)-1-(2-fluorophenyl)-2-hydroxyethyl]-4-isopropylbenzamide; compound with trifluoroacetic acid

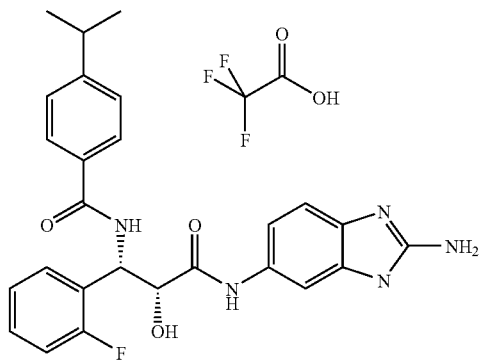

Ethoxycarbonylmethyltriphenylphosphonium bromide was prepared according to German patent application 4238260 and tertiary-butyl 2,5-diaminobenzimidazole-1-carboxylate was prepared according to International application WO2002/042273.

Process Step 1

Isopropyl E-3-(2-fluorophenyl)acrylate

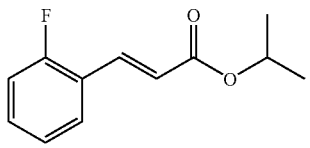

400 mg of sodium hydride (60% in oil, 10 mmol) were added to a stirred solution of 4.4 g of ethoxycarbonylmethyl-triphenylphosphonium bromide (10 mmol) in 20 ml of DMF and the mixture was stirred further at RT for 10 min. 1.24 g of 2-fluoro-benzaldehyde (10 mmol) were added and the mixture was stirred for 5 h at RT. The reaction mixture was taken up in 100 ml of ethyl acetate and washed with a common salt solution, dried over sodium sulfate, filtered and concentrated under reduced pressure. Purification took place using a silica gel chromatography (ethyl acetate/heptane 1:1). 1.25 g of the title compound were obtained. Yield: 60%.

LC/MS (Method D) (M+H)+ 209.

Process Step 2

Isopropyl (1S,2R)-3-acetylamino-3-(2-fluorophenyl)-2-hydroxypropionate 1.25 g of the compound obtained from Process step 1 (6 mmol) were reacted analogously to the preparation of Example 4, Process step 2. 1.18 g of the title compound were obtained; yield: 69%.

LC/MS (Method D) (M+H)+ 284

Process Step 3

(1S,2R)-3-Amino-3-(2-fluorophenyl)-2-hydroxypropionic acid; compound with hydrochloric acid 1.18 g of the compound obtained from Process step 2 (4.11 mmol) were reacted analogously to the preparation of Example 4, Process step 3. 1 g of the title compound was obtained; yield: 99%.

LC/MS (Method D) (M+H)+ 200

Process Step 4

(2R,3S)-3-(2-Fluorophenyl)-2-hydroxy-3-(4-isopropylbenzoylamino)propionic acid 342 mg of 4-isopropylbenzoic acid (2.1 mmol) and 416 mg of the process product from step 3 (2.1 mmol) were reacted analogously to Example 4, Process step 4. 365 mg of the title compound were obtained as a white solid; yield: 50%.

LC/MS (Method D) (M+H)+ 346

Process Step 5 tertiary-Butyl (2R,3S)-2-amino-5-[3-(2-fluorophenyl)-2-hydroxy-3-(4-isopropylbenzoylamino)propionylamino]benzimidazole-1-carboxylate

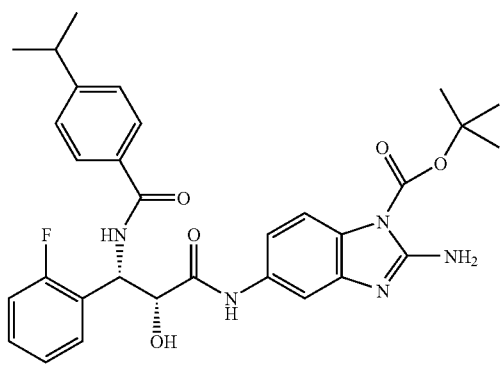

65 mg of tertiary-butyl 2,5-diaminobenzimidazole-1-carboxylate and 92 mg of the compound obtained from Process step 4 (0.266 mmol) were dissolved in 2 ml of DMF. Subsequently, 36 mg of HOAt (0.265 mmol), 130 mg of PyBrop (0.28 mmol) and 200 µl of DIPEA (1.17 mmol) in 1 ml DMF were added. After stirring at RT for 3 h, the mixture was diluted with ethyl acetate. The organic phase was washed with a common salt solution, dried over sodium sulfate, filtered and concentrated under reduced pressure. The crude product was employed without further purification in the next process step. LC/MS (Method D) (M+H)+ 576

Process Step 6

N-[(1S,2R)-2-(2-Amino-3H-benzimidazol-5-ylcarbamoyl)-1-(2-fluorophenyl)-2-hydroxyethyl]-4-isopropylbenzamide; compound with trifluoroacetic acid The residue from Process step 5 was dissolved in a mixture of 2 ml of DCM and 2 ml of TFA. After stirring at RT for 2 h, the solvent was evaporated under reduced pressure and the residue was purified using preparative HPLC. 65 mg of the title compound were obtained as a white solid; yield: 44%.

LC/MS (Method A) 475.20 ($R_t$=1.38 min, 100%)

$^1$H NMR (400 MHz, DMSO-$d_6$) δ (ppm): 1.19 (d, 6H), 2.92 (hept, 1H), 4.40 (s br, 1H), 5.79 (dd, 1H), 6.38 (s br, 1H), 7.14-7.38 (m, 8H), 7.52 (dt, 1H), 7.77 (d, 2H), 7.88 (s, 1H), 8.40 (s, 1H), 8.43 (d, 1H), 10.00 (s, 1H) 12.40 (s br, 1H)

Example 7

N-[(1S,2R)-[2-(2-Amino-3H-benzimidazol-5-ylcarbamoyl)-2-hydroxy-1-phenylethyl]-4-tertiary-butyl-benzamide; compound with trifluoroacetic acid

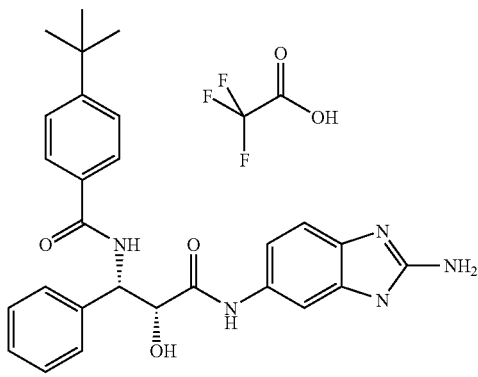

Process Step 1 tertiary-Butyl (1S,2R)-2-amino-6-(3-tert-butoxycarbonylamino-2-hydroxy-3-phenyl-propionylamino)benzimidazole-1-carboxylate

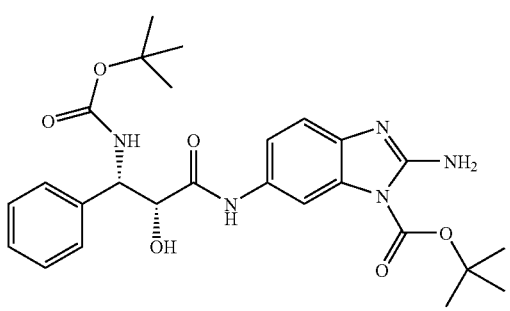

1.5 g of (1S,2R)-3-tertiary-butoxycarbonylamino-2-hydroxy-3-phenylpropionic acid (5.3 mmol) and 1.32 g of tertiary-butyl 2,5-diaminobenzimidazole-1-carboxylate (5.3 mmol) were dissolved in 30 ml of DMF. 798 mg of HOAt (5.86 mmol), 1.75 g of PyBrop (5.86 mmol) and 2.8 ml of DIPEA (16 mmol) in 15 ml of DCM and 15 ml of DMF were added and the mixture was stirred at RT for 5 h. The organic phase was washed with aqueous sodium hydrogencarbonate solution and common salt solution, dried over sodium sulfate, filtered and concentrated under reduced pressure. After silica gel chromatography (ethyl acetate/heptane 2:1), 2 g of the title compound were obtained as a white solid. Yield: 74%.

LC/MS (Method D) (M+H-tBu)$^+$ 456

Process Step 2

(1S,2R)-3-Amino-N-(2-amino-3H-benzimidazol-5-yl)-2-hydroxy-3-phenylpropionamide; compound with trifluoroacetic acid

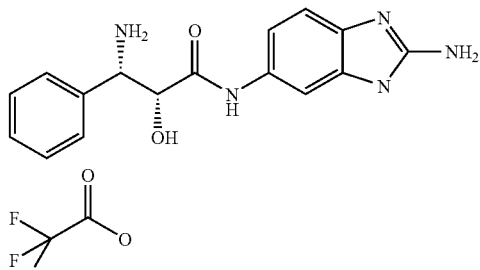

The process product from step 1 was dissolved in 10 ml of DCM and 10 ml of TFA, stirred for 2 h at RT and 2.1 g of the title compound were obtained as a pink solid; yield 99%.

LC/MS (Method D) (M+H)$^+$ 312

Process Step 3

N-[(1S,2R)-[2-(2-Amino-3H-benzimidazol-5-ylcarbamoyl)-2-hydroxy-1-phenylethyl]-4-tertiary-butyl-benzamide; compound with trifluoroacetic acid 45 mg of 4-tertiary-butylbenzoic acid (0.25 mmol), 91 mg of TOTU (0.28 mmol) and 150 µl of N-ethylmorpholine (1.5 mmol) were dissolved in 2 ml of DMF and the solution was stirred for 30 min at RT. 132 mg of the process product from step 2 (0.25 mmol) were added and the mixture was stirred for 2 h at RT. The mixture was diluted with ethyl acetate. The organic phase was washed with aqueous sodium hydrogencarbonate solution and common salt solution, dried over sodium sulfate, filtered and concentrated under reduced pressure. The residue was purified by means of HPLC. 36 mg of the title compound were obtained as a white solid. Yield: 25%.

LC/MS (Method A) 472.31 (R$_t$=1.39 min, 100%)

$^1$H NMR (400 MHz, DMSO-d$_6$) δ (ppm): 1.29 (s, 9H), 4.47 (s br, 1H), 5.50 (dd, 1H), 6.11 (s br, 1H), 7.20-7.35 (m, 5H), 7.40-7.48 (m, 5H), 7.76 (d, 2H), 7.85 (s, 1H), 8.39 (s br, 1H), 8.45 (d, 1H), 8.39 (d, 1H), 9.99 (s, 1H).

29

Example 8

N-[(1S,2R)-2-(4-Aminomethylphenylcarbamoyl)-2-hydroxy-1-phenylethyl]benzamide; compound with trifluoroacetic acid

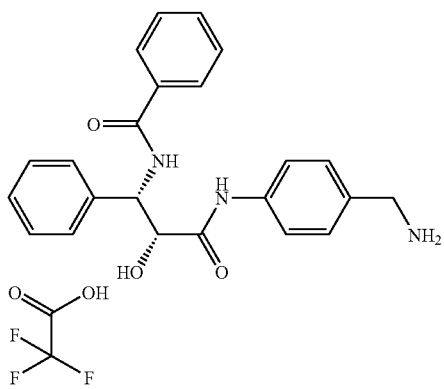

Process Step 1 tert-Butyl[4-((2R,3S)-3-benzoylamino-2-hydroxy-3-phenylpropionylamino)benzyl]-carbamate

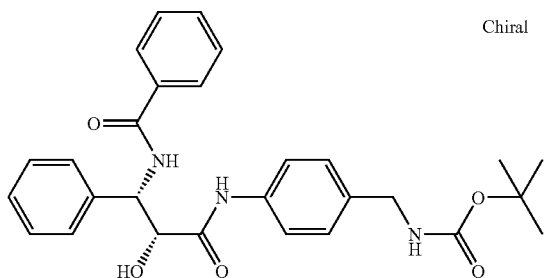

Analogously to Example 1, Process step 1, 33 mg (0.15 mmol) of tert-butyl (4-aminobenzyl)carbamate and 43 mg (0.15 mmol) of (2R,3S)-3-benzoylamino-2-hydroxy-3-phenylpropionic acid were dissolved in 1 ml of DCM and 1 ml of DMF and treated successively with 78 µl of DIPEA (0.45 mmol), 22.5 mg of HOAt (0.165 mmol) and 76.9 mg (0.165 mmol) of PyBrop. Without further work-up, the batch obtained was filtered and then purified using HPLC. The product-containing fractions were lyophilized.

30

Process Step 2

N-[(1S,2R)-2-(4-Aminomethylphenylcarbamoyl)-2-hydroxy-1-phenylethyl]benzamide; compound with trifluoroacetic acid

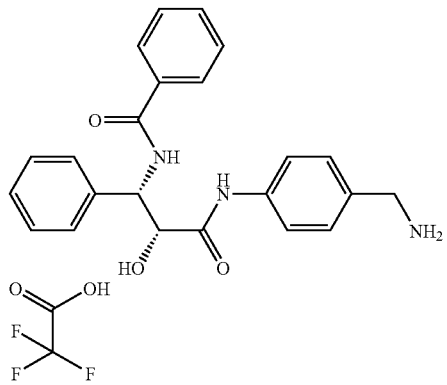

The process product from step 1 was reacted analogously to Example 1; Process step 3; the mixture was then concentrated, treated with water and lyophilized.

Yield: 31.5 mg (43% over 2 stages).

LC/MS (Method A) M-NH$_2$=373.40 (R$_t$=1.09 min, 85%)

$^1$H NMR (500 MHz, DMSO-d$_6$) δ (ppm): 3.97 (d, 2H), 4.47 (s br, 1H), 5.50 (dd, 1H), 6.11 (dd, 1H), 7.23 (m, 1H), 7.30-7.36 (m, 4H), 7.42-7.48 (m, 4H), 7.53 (m, 1H), 7.62 (d, 2H), 7.84 (d, 2H), 8.05 (s br, 3H), 8.53 (d, 1H), 9.99 (s, 1H).

Example 9

N-[(1S,2R)-2-(2,4-Diaminoquinazolin-6-ylcarbamoyl)-2-hydroxy-1-phenylethyl]benzamide; compound with trifluoroacetic acid

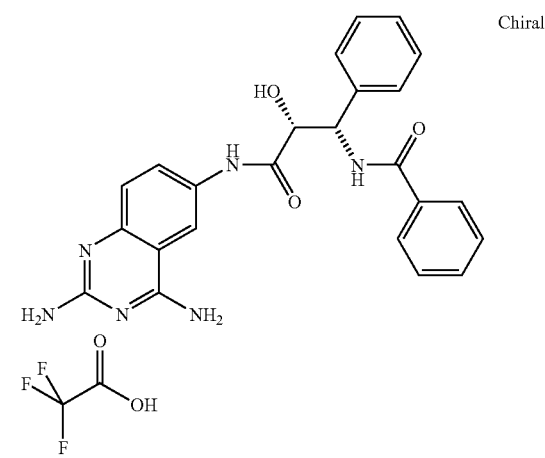

Analogously to Example 1, Process step 1, 76 mg (0.44 mmol) of quinazoline-2,4,6-triamine and 150 mg (0.52 mmol) of (2R,3S)-3-benzoylamino-2-hydroxy-3-phenylpropionic acid were dissolved in 3 ml of DMF and treated successively with 153 µl of DIPEA (0.86 mmol), 78.9 mg of HOAt (0.57 mmol) and 251 mg (0.53 mmol) of PyBrop.

Without further work-up, the batch was filtered and purified using HPLC. The product-containing phases were lyophilized.

Yield: 114 mg (48%).

LC/MS (Method A) M+H=443.32 ($R_t$=1.10 min, 100%)

$^1$H NMR (500 MHz, DMSO-$d_6$) δ (ppm): 4.51 (m, 1H), 5.54 (m, 1H), 6.25 (d, 1H), 7.22-7.51 (m, 9H), 7.75-7.83 (m, 4H), 8.36 (s br, 1H), 8.53 (d, 1H), 8.72 (s br, 1H), 8.93 (s br, 1H), 10.15 (s br, 1H), 12.30 (s br, 1H).

The compounds in Table 1 below were prepared analogously to the above examples.

The representation of the compounds was carried out according to the rules of the International Union for Pure and Applied Chemistry (IUPAC). The absolute stereo-chemistry was not indicated and the compounds were in each case prepared as salts of trifluoroacetic acid.

TABLE 1

| Example No. | Compound | Mass from LC-MS | $R_t$ from LC-MS | LC-MS method |
|---|---|---|---|---|
| 10 | 4-Amino-N-[2-(2-amino-3H-benzimidazol-5-ylcarbamoyl)-2-hydroxy-1-phenylethyl]benzamide | 431.23 | 0.81 | A |
| 11 | Quinoxaline-2-carboxylic acid [2-(2-amino-3H-benzimidazol-5-ylcarbamoyl)-2-hydroxy-1-phenyl-ethyl]amide | 468.23 | 1.14 | A |
| 12 | N-[2-(2-Amino-3H-benzimidazol-5-ylcarbamoyl)-2-hydroxy-1-phenylethyl]-4-methoxybenzamide | 446.23 | 1.08 | A |
| 13 | Thiophene-3-carboxylic acid [2-(2-amino-3H-benzimidazol-5-ylcarbamoyl)-2-hydroxy-1-phenyl-ethyl]amide | 422.17 | 1 | A |
| 14 | 1-Methyl-1H-pyrrole-2-carboxylic acid [(1S,2R)-2-(2-amino-3H-benzimidazol-5-ylcarbamoyl)-2-hydroxy-1-phenylethyl]amide | 419.23 | 1.02 | A |
| 15 | Quinoline-2-carboxylic acid [2-(2-amino-3H-benzimidazol-5-ylcarbamoyl)-2-hydroxy-1-phenyl-ethyl]amide | 467.23 | 1.23 | A |
| 16 | N-[2-(2-Amino-3H-benzimidazol-5-ylcarbamoyl)-2-hydroxy-1-phenylethyl]-4-cyclohexylbenzamide | 498.23 | 1.5 | A |
| 17 | N-[2-(2-Amino-3H-benzimidazol-5-ylcarbamoyl)-2-hydroxy-1-phenylethyl]-4-isopropylbenzamide | 458.2 | 1.33 | A |
| 18 | N-[2-(2-Amino-3H-benzimidazol-5-ylcarbamoyl)-2-hydroxy-1-phenylethyl]-4-trifluoromethoxy-benzamide | 500.11 | 1.33 | A |
| 19 | N-[2-(2-Amino-3H-benzimidazol-5-ylcarbamoyl)-2-hydroxy-1-phenylethyl]-4-diethylaminobenzamide | 487.28 | 1 | A |
| 20 | N-[2-(2-Amino-3H-benzimidazol-5-ylcarbamoyl)-2-hydroxy-1-phenylethyl]-4-phenoxybenzamide | 508.24 | 1.4 | A |
| 21 | N-[2-(2-Amino-3H-benzimidazol-5-ylcarbamoyl)-2-hydroxy-1-phenylethyl]-4-benzylbenzamide | 506.27 | 1.41 | A |
| 22 | N-[2-(2-Amino-3H-benzimidazol-5-ylcarbamoyl)-2-hydroxy-1-phenylethyl]-4-isopropoxybenzamide | 474.27 | 1.47 | B |
| 23 | N-[2-(2-Amino-3H-benzimidazol-5-ylcarbamoyl)-2-hydroxy-1-phenylethyl]-4-methylsulfanyl-benzamide | 462.22 | 1.37 | B |
| 24 | N-[2-(2-Amino-3H-benzimidazol-5-ylcarbamoyl)-2-hydroxy-1-phenylethyl]-4-ethylsulfanylbenzamide | 476.23 | 1.44 | B |
| 25 | N-[2-(2-Amino-3H-benzimidazol-5-ylcarbamoyl)-2-hydroxy-1-phenylethyl]-4-[(4,6-dimethylpyrimidin-2-yl)methylamino]benzamide | 551.32 | 1.18 | B |
| 26 | N-[2-(2-Amino-3H-benzimidazol-5-ylcarbamoyl)-2-hydroxy-1-phenylethyl]-4-pyridin-3-ylbenzamide | 493.26 | 0.95 | B |
| 27 | 4-(2-Acetylamino-3,3,3-trifluoropropyl)-N-[2-(2-amino-3H-benzimidazol-5-ylcarbamoyl)-2-hydroxy-1-phenylethyl]benzamide | 569.29 | 1.32 | B |
| 28 | 1-Methyl-1H-indole-2-carboxylic acid [2-(2-amino-3H-benzimidazol-5-ylcarbamoyl)-2-hydroxy-1-phenylethyl]amide | 469.26 | 1.45 | B |
| 29 | 5-Methoxy-1H-indole-2-carboxylic acid [2-(2-amino-3H-benzimidazol-5-ylcarbamoyl)-2-hydroxy-1-phenylethyl]amide | 485.26 | 1.36 | B |
| 30 | 5-Ethyl-1H-indole-2-carboxylic acid [2-(2-amino-3H-benzimidazol-5-ylcarbamoyl)-2-hydroxy-1-phenylethyl]amide | 483.28 | 1.58 | B |
| 31 | 6-Methoxy-1H-indole-2-carboxylic acid [2-(2-amino-3H-benzimidazol-5-ylcarbamoyl)-2-hydroxy-1-phenylethyl]amide | 485.26 | 1.39 | B |
| 32 | 4-Methoxyquinoline-2-carboxylic acid [2-(2-amino-3H-benzimidazol-5-ylcarbamoyl)-2-hydroxy-1-phenylethyl]amide | 497.25 | 1.5 | B |
| 33 | 3-Ethoxyquinoxaline-2-carboxylic acid [2-(2-amino-3H-benzimidazol-5-ylcarbamoyl)-2-hydroxy-1-phenylethyl]amide | 512.27 | 1.45 | B |

TABLE 1-continued

| Example No. | Compound | Mass from LC-MS | R$_t$ from LC-MS | LC-MS method |
|---|---|---|---|---|
| 34 | Naphthalene-2-carboxylic acid [2-(2-amino-3H-benzimidazol-5-ylcarbamoyl)-2-hydroxy-1-phenyl-ethyl]amide | 466.24 | 1.29 | A |
| 35 | N-[2-(2-Amino-3H-benzimidazol-5-ylcarbamoyl)-2-hydroxy-1-phenylethyl]-4-pyrrol-1-ylbenzamide | 481.26 | 1.3 | A |
| 36 | N-[2-(2-Amino-3H-benzimidazol-5-ylcarbamoyl)-2-hydroxy-1-phenylethyl]-4-trifluoromethylsulfanyl-benzamide | 516.17 | 1.39 | A |
| 37 | Biphenyl-4-carboxylic acid [2-(2-amino-3H-benzimidazol-5-ylcarbamoyl)-2-hydroxy-1-phenyl-ethyl]amide | 492.28 | 1.53 | B |
| 38 | N-[2-(2-Amino-3H-benzimidazol-5-ylcarbamoyl)-2-hydroxy-1-phenylethyl]-4-(2,2,2-trifluoroethoxy)-benzamide | 514.25 | 1.44 | B |
| 39 | Benzyl [2-(2-amino-3H-benzimidazol-5-ylcarbamoyl)-2-hydroxy-1-phenylethyl]carbamate | 446.25 | 1.27 | A |
| 40 | N-[2-(2-Amino-3H-benzimidazol-5-ylcarbamoyl)-2-hydroxy-1-phenylethyl]-4-ethylbenzamide | 444.23 | 1.4 | B |
| 41 | N-[2-(2-Amino-3H-benzimidazol-5-ylcarbamoyl)-2-hydroxy-1-phenylethyl]-4-ethoxybenzamide | 460.22 | 1.31 | B |
| 42 | 5-Butylpyridine-2-carboxylic acid [2-(2-amino-3H-benzimidazol-5-ylcarbamoyl)-2-hydroxy-1-phenyl-ethyl]amide | 473.24 | 1.62 | B |
| 43 | Benzo[b]thiophene-2-carboxylic acid [2-(2-amino-3H-benzimidazol-5-ylcarbamoyl)-2-hydroxy-1-phenylethyl]amide | 472.17 | 1.42 | B |
| 44 | 6-Methoxynaphthalene-2-carboxylic acid [2-(2-amino-3H-benzimidazol-5-ylcarbamoyl)-2-hydroxy-1-phenylethyl]amide | 496.22 | 1.45 | B |
| 45 | 4-(2,2,2-Trifluoroethyl)-4H-thieno[3,2-b]pyrrole-5-carboxylic acid [2-(2-amino-3H-benzimidazol-5-ylcarbamoyl)-2-hydroxy-1-phenylethyl]amide | 543.17 | 1.54 | B |
| 46 | Biphenyl-3,4'-dicarboxylic acid 4'-{[2-(2-amino-3H-benzimidazol-5-ylcarbamoyl)-2-hydroxy-1-phenyl-ethyl]amide} 3-methylamide | 549.26 | 1.28 | B |
| 47 | N-[2-(1-Aminoisoquinolin-7-ylcarbamoyl)-2-hydroxy-1-phenylethyl]-4-diethylaminobenzamide | 497.24 | 1.09 | A |
| 48 | N-[2-(1-Aminoisoquinolin-7-ylcarbamoyl)-2-hydroxy-1-phenylethyl]-4-isopropylbenzamide | 468.22 | 1.37 | A |
| 49 | N-[2-(1-Aminoisoquinolin-7-ylcarbamoyl)-2-hydroxy-1-phenylethyl]-6-pyrrolidin-1-yl-nicotinamide | 496.22 | 1.03 | A |
| 50 | N-[2-(1-Aminoisoquinolin-7-ylcarbamoyl)-2-hydroxy-1-phenylethyl]-4-morpholin-4-yl-benzamide | 511.22 | 1.16 | A |
| 51 | N-[2-(1-Aminoisoquinolin-7-ylcarbamoyl)-2-hydroxy-1-phenylethyl]-4-pyrrol-1-ylbenzamide | 491.2 | 1.37 | A |
| 52 | 1-Ethyl-2,3-dimethyl-1H-indole-5-carboxylic acid [2-(2-amino-3H-benzimidazol-5-ylcarbamoyl)-2-hydroxy-1-phenylethyl]amide | 511.35 | 1.4 | A |
| 53 | N-[2-(2-Amino-3H-benzimidazol-5-ylcarbamoyl)-2-hydroxy-1-phenylethyl]-4-morpholin-4-yl-benzamide | 501.33 | 1.2 | A |
| 54 | N-[2-(1-Aminoisoquinolin-7-ylcarbamoyl)-2-hydroxy-1-phenylethyl]-4-pyrrolidin-1-yl-benzamide | 495.23 | 1.34 | A |
| 55 | N-[2-(1-Aminoisoquinolin-7-ylcarbamoyl)-2-hydroxy-1-phenylethyl]-6-morpholin-4-yl-nicotinamide | 513.22 | 0.97 | A |
| 56 | 5,6-Dimethoxy-1H-indole-2-carboxylic acid [2-(2-amino-3H-benzimidazol-5-ylcarbamoyl)-2-hydroxy-1-phenylethyl]amide | 515.34 | 1.16 | A |
| 57 | N-[2-(2-Amino-3H-benzimidazol-5-ylcarbamoyl)-2-hydroxy-1-phenylethyl]-4-pyrrolidin-1-yl-benzamide | 485.11 | 1.37 | A |
| 58 | N-[2-(2-Amino-3H-benzimidazol-5-ylcarbamoyl)-2-hydroxy-1-phenylethyl]-4-isobutylbenzamide | 472.3 | 1.65 | B |
| 59 | N-[2-(2-Amino-3H-benzimidazol-5-ylcarbamoyl)-2-hydroxy-1-phenylethyl]-4-butylbenzamide | 472.3 | 1.67 | B |
| 60 | N-[2-(2-Amino-3H-benzimidazol-5-ylcarbamoyl)-2-hydroxy-1-phenylethyl]-4-propylbenzamide | 458.28 | 1.36 | A |
| 61 | 4H-Thieno[3,2-b]pyrrole-5-carboxylic acid [2-(2-amino-3H-benzimidazol-5-ylcarbamoyl)-2-hydroxy-1-phenylethyl]amide | 461.2 | 1.3 | B |

TABLE 1-continued

| Example No. | Compound | Mass from LC-MS | $R_t$ from LC-MS | LC-MS method |
|---|---|---|---|---|
| 62 | N-[2-(4-Carbamimidoylphenylcarbamoyl)-2-hydroxy-1-phenylethyl]-4-diethylaminobenzamide | 473.24 | 0.98 | A |
| 63 | 5-Methoxy-1H-indole-2-carboxylic acid [2-(1-aminoisoquinolin-7-ylcarbamoyl)-2-hydroxy-1-phenylethyl]amide | 495.19 | 1.32 | A |
| 64 | 5-Ethylthiophene-2-carboxylic acid [2-(1-amino-isoquinolin-7-ylcarbamoyl)-2-hydroxy-1-phenyl-ethyl]amide | 460.16 | 1.31 | A |
| 65 | 5-tert-Butylthiophene-2-carboxylic acid [2-(1-aminoisoquinolin-7-ylcarbamoyl)-2-hydroxy-1-phenylethyl]amide | 488.19 | 1.45 | A |
| 66 | N-[2-(1-Aminoisoquinolin-6-ylcarbamoyl)-2-hydroxy-1-phenylethyl]benzamide | 426.17 | 1.15 | A |
| 67 | 6-Bromobenzofuran-2-carboxylic acid [2-(2-amin-3H-benzimidazol-5-ylcarbamoyl)-2-hydroxy-1-phenylethyl]amide | 534.15 | 1.37 | A |
| 68 | 5-Ethylthiophene-2-carboxylic acid [2-(2-amino-3H-benzimidazol-5-ylcarbamoyl)-2-hydroxy-1-phenylethyl]amide | 450.16 | 1.25 | A |
| 69 | Thieno[3,2-b]thiophene-2-carboxylic acid [2-(2-amino-3H-benzimidazol-5-ylcarbamoyl)-2-hydroxy-1-phenylethyl]amide | 478.15 | 1.3 | A |
| 70 | 5-Methoxybenzofuran-2-carboxylic acid [2-(2-amin-3H-benzimidazol-5-ylcarbamoyl)-2-hydroxy-1-phenylethyl]amide | 486.2 | 1.26 | A |
| 71 | Benzo[b]thiophene-3-carboxylic acid [2-(2-amino-3H-benzimidazol-5-ylcarbamoyl)-2-hydroxy-1-phenylethyl]amide | 472.17 | 1.26 | A |
| 72 | 4-Methylthiophene-2-carboxylic acid [2-(2-amino-3H-benzimidazol-5-ylcarbamoyl)-2-hydroxy-1-phenylethyl]amide | 436.14 | 1.18 | A |
| 73 | N-[2-(2-Aminobenzothiazol-6-ylcarbamoyl)-2-hydroxy-1-phenylethyl]-4-diethylaminobenzamide; compound with trifluoroacetic acid | 503.2 | 1.42 | A |
| 74 | 1H-Indole-2-carboxylic acid [2-(2-amino-3H-benzimidazol-5-ylcarbamoyl)-2-hydroxy-1-phenyl-ethyl]amide | 455.22 | 1.21 | A |
| 75 | N-[2-(2-Amino-3H-benzimidazol-5-ylcarbamoyl)-2-hydroxy-1-phenylethyl]-4-dimethylamino-benzamide; compound with trifluoroacetic acid | 459.25 | 1.06 | A |
| 76 | 5-tert-Butylthiophene-2-carboxylic acid [2-(2-amino-3H-benzimidazol-5-ylcarbamoyl)-2-hydroxy-1-phenylethyl]amide | 478.2 | 1.38 | A |
| 77 | N-[2-(2-Amino-3H-benzimidazol-5-ylcarbamoyl)-2-hydroxy-1-phenylethyl]-4-methoxy-3-methyl-benzamide | 460.19 | 1.2 | A |
| 78 | N-[2-(2-Amino-3H-benzimidazol-5-ylcarbamoyl)-2-hydroxy-1-phenylethyl]-3-fluoro-4-methyl-benzamide | 448.17 | 1.22 | A |
| 79 | 5-Isopropylthiophene-3-carboxylic acid [2-(2-amino-3H-benzimidazol-5-ylcarbamoyl)-2-hydroxy-1-phenylethyl]amide | 464.15 | 1.31 | A |
| 80 | 5-Ethylthiophene-3-carboxylic acid [2-(2-amino-3H-benzimidazol-5-ylcarbamoyl)-2-hydroxy-1-phenylethyl]amide | 450.12 | 1.24 | A |
| 81 | [2,2']Bithiophenyl-5-carboxylic acid [2-(2-amino-3H-benzimidazol-5-ylcarbamoyl)-2-hydroxy-1-phenylethyl]amide | 504.14 | 1.35 | A |
| 82 | 5-Methoxy-1H-indole-2-carboxylic acid [2-(1-aminoisoquinolin-6-ylcarbamoyl)-2-hydroxy-1-phenylethyl]amide; compound with trifluoroacetic acid | 495.19 | 1.26 | A |
| 83 | N-[2-(1-Aminoisoquinolin-6-ylcarbamoyl)-2-hydroxy-1-phenylethyl]-4-methoxybenzamide | 456.18 | 1.19 | A |
| 84 | N-[2-(1-Aminoisoquinolin-6-ylcarbamoyl)-2-hydroxy-1-phenylethyl]-4-isopropylbenzamide | 468.22 | 1.38 | A |
| 85 | N-[2-(1-Aminoisoquinolin-6-ylcarbamoyl)-2-hydroxy-1-phenylethyl]-4-diethylaminobenzamide | 497.24 | 1.05 | A |
| 86 | N-[2-(1-Aminoisoquinolin-6-ylcarbamoyl)-2-hydroxy-1-phenylethyl]-4-ethoxybenzamide | 470.2 | 1.32 | A |
| 87 | N-[2-(1-Aminoisoquinolin-6-ylcarbamoyl)-2-hydroxy-1-phenylethyl]-4-ethylbenzamide | 454.2 | 1.37 | A |
| 88 | N-[2-(1-Aminoisoquinolin-6-ylcarbamoyl)-2-hydroxy-1-phenylethyl]-4-tert-butylbenzamide | 482.23 | 1.43 | A |

TABLE 1-continued

| Example No. | Compound | Mass from LC-MS | $R_t$ from LC-MS | LC-MS method |
|---|---|---|---|---|
| 89 | N-[2-(1-Aminoisoquinolin-6-ylcarbamoyl)-2-hydroxy-1-phenylethyl]-3-dimethylamino-benzamide | 469.21 | 0.97 | A |
| 90 | N-[2-(1-Aminoisoquinolin-6-ylcarbamoyl)-2-hydroxy-1-phenylethyl]-4-dimethylamino-benzamide | 469.21 | 1.13 | A |
| 91 | 5-Ethylthiophene-2-carboxylic acid [2-(1-amino-isoquinolin-6-ylcarbamoyl)-2-hydroxy-1-phenyl-ethyl]amide | 460.16 | 1.32 | A |
| 92 | 5-Ethylthiophene-3-carboxylic acid [2-(1-amino-isoquinolin-6-ylcarbamoyl)-2-hydroxy-1-phenyl-ethyl]amide | 460.16 | 1.31 | A |
| 93 | 5-tert-Butylthiophene-2-carboxylic acid [2-(1-aminoisoquinolin-6-ylcarbamoyl)-2-hydroxy-1-phenylethyl]amide | 488.19 | 1.43 | A |
| 94 | N-[2-(1-Aminoisoquinolin-6-ylcarbamoyl)-2-hydroxy-1-phenylethyl]-3-ethylbenzamide | 454.2 | 1.36 | A |
| 95 | N-[2-(1-Aminoisoquinolin-6-ylcarbamoyl)-2-hydroxy-1-phenylethyl]-3-ethoxybenzamide | 470.2 | 1.33 | A |
| 96 | N-[2-(2-Amino-1H-benzimidazol-5-ylcarbamoyl)-2-hydroxy-1-(3-trifluoromethylphenyl)ethyl]-4-iso-propylbenzamide | 526.19 | 1.53 | A |
| 97 | N-[2-(2-Amino-1H-benzimidazol-5-ylcarbamoyl)-2-hydroxy-1-(2-methoxyphenyl)ethyl]-4-isopropyl-benzamide | 488.35 | 1.4 | A |
| 98 | N-[2-(2-Amino-1H-benzimidazol-5-ylcarbamoyl)-2-hydroxy-1-(3-trifluoromethylphenyl)ethyl]-4-diethyl-aminobenzamide | 555.39 | 1.23 | A |
| 99 | N-[2-(2-Amino-1H-benzimidazol-5-ylcarbamoyl)-2-hydroxy-1-(2-methoxyphenyl)ethyl]-4-diethyl-aminobenzamide | 517.41 | 1.1 | A |
| 100 | N-[2-(2-Amino-1H-benzimidazol-5-ylcarbamoyl)-2-hydroxy-1-(4-methoxyphenyl)ethyl]-4-ethyl-aminobenzamide | 517.42 | 1.03 | A |
| 101 | N-[2-(1-Aminoisoquinolin-6-ylcarbamoyl)-1-(3-ethoxyphenyl)-2-hydroxyethyl]-4-diethyl-aminobenzamide | 541.27 | 1.28 | B |
| 102 | N-[2-(2-Amino-3H-benzimidazol-5-ylcarbamoyl)-2-hydroxy-1-(4-isopropylphenyl)ethyl]-4-diethyl-aminobenzamide | 529.24 | 1.28 | A |
| 103 | N-[2-(2-Amino-3H-benzimidazol-5-ylcarbamoyl)-1-(3-ethoxyphenyl)-2-hydroxyethyl]-4-isopropyl-benzamide | 502.16 | 1.46 | A |
| 104 | N-[2-(2-Amino-3H-benzimidazol-5-ylcarbamoyl)-1-(3-ethoxyphenyl)-2-hydroxyethyl]-4-diethylamino-benzamide | 531.24 | 1.16 | A |
| 105 | N-[2-(1-Aminoisoquinolin-6-ylcarbamoyl)-2-hydroxy-1-m-tolylethyl]-4-diethylaminobenzamide | 511.26 | 1.15 | A |
| 106 | N-[2-(2-Amino-3H-benzimidazol-5-ylcarbamoyl)-2-hydroxy-1-(4-isopropylphenyl)ethyl]-4-isopropyl-benzamide | 500.19 | 1.55 | A |
| 107 | N-[2-(2-Aminobenzothiazol-6-ylcarbamoyl)-2-hydroxy-1-(4-trifluoromethylphenyl)ethyl]-4-iso-propylbenzamide | 542.16 | 1.53 | A |
| 108 | N-[2-(2-Aminobenzothiazol-6-ylcarbamoyl)-2-hydroxy-1-m-tolylethyl]-4-diethylaminobenzamide | 517.21 | 1.14 | A |
| 109 | N-[2-(2-Aminobenzothiazol-6-ylcarbamoyl)-2-hydroxy-1-m-tolylethyl]-4-isopropylbenzamide | 488.19 | 1.42 | A |
| 110 | N-[2-(2-Aminobenzothiazol-6-ylcarbamoyl)-2-hydroxy-1-(4-isopropylphenyl)ethyl]-4-diethyl-aminobenzamide | 545.25 | 1.27 | A |
| 111 | N-[2-(2-Aminobenzothiazol-6-ylcarbamoyl)-1-(3-ethoxy-phenyl)-2-hydroxyethyl]-4-diethylamino-benzamide | 547.23 | 1.13 | A |
| 112 | N-[2-(2-Aminobenzothiazol-6-ylcarbamoyl)-2-hydroxy-1-(4-trifluoromethylphenyl)ethyl]-4-diethyl-aminobenzamide | 571.19 | 1.27 | A |
| 113 | N-[2-(2-Amino-3H-benzimidazol-5-ylcarbamoyl)-1-(2-chlorophenyl)-2-hydroxyethyl]-4-diethylamino-benzamide | 521.19 | 1.06 | A |
| 114 | N-[2-(2-Amino-3H-benzimidazol-5-ylcarbamoyl)-2-hydroxy-1-(4-trifluoromethylphenyl)ethyl]-4-iso-propylbenzamide | 526.14 | 1.5 | A |

TABLE 1-continued

| Example No. | Compound | Mass from LC-MS | R$_t$ from LC-MS | LC-MS method |
|---|---|---|---|---|
| 115 | N-[2-(2-Amino-3H-benzimidazol-5-ylcarbamoyl)-2-hydroxy-1-(4-trifluoromethylphenyl)ethyl]-4-diethylaminobenzamide | 555.24 | 1.29 | A |
| 116 | N-[2-(2-Aminobenzothiazol-6-ylcarbamoyl)-1-(3-ethoxyphenyl)-2-hydroxyethyl]-4-isopropylbenzamide | 518.2 | 1.46 | A |
| 117 | N-[2-(2-Aminobenzothiazol-6-ylcarbamoyl)-1-(2-chlorophenyl)-2-hydroxyethyl]-4-diethylaminobenzamide | M + 1 = 538/540 | 0.93 | D |
| 118 | N-[2-(1-Aminoisoquinolin-6-ylcarbamoyl)-1-(3-bromophenyl)-2-hydroxyethyl]-4-diethylaminobenzamide | 575.15 | 1.35 | B |
| 119 | N-[2-(1-Aminoisoquinolin-6-ylcarbamoyl)-1-(3-bromophenyl)-2-hydroxyethyl]-4-ethylbenzamide | 532.11 | 1.63 | B |
| 120 | N-[2-(1-Aminoisoquinolin-6-ylcarbamoyl)-2-hydroxy-1-(4-isopropylphenyl)ethyl]-4-isopropylbenzamide | 510.26 | 1.58 | A |
| 121 | N-[2-(1-Aminoisoquinolin-6-ylcarbamoyl)-1-(2-chlorophenyl)-2-hydroxyethyl]-4-isopropylbenzamide | 502.18 | 1.44 | B |
| 122 | N-[2-(2-Amino-3H-benzimidazol-5-ylcarbamoyl)-2-hydroxy-1-m-tolylethyl]-4-isopropylbenzamide | 472.18 | 1.42 | A |
| 123 | N-[2-(2-Amino-3H-benzimidazol-5-ylcarbamoyl)-2-hydroxy-1-m-tolylethyl]-4-diethylaminobenzamide | 501.23 | 1.09 | A |
| 124 | N-[2-(1-Aminoisoquinolin-6-ylcarbamoyl)-1-(4-bromophenyl)-2-hydroxyethyl]-4-diethylaminobenzamide | 575.15 | 1.37 | B |
| 125 | N-[2-(1-Aminoisoquinolin-6-ylcarbamoyl)-1-(4-bromophenyl)-2-hydroxyethyl]-4-isopropylbenzamide | M + 1 = 547/548 | 1.24 | D |
| 126 | N-[2-(1-Aminoisoquinolin-6-ylcarbamoyl)-1-(3-bromophenyl)-2-hydroxyethyl]-4-isopropylbenzamide | 546.13 | 1.66 | C |
| 127 | N-[2-(1-Aminoisoquinolin-6-ylcarbamoyl)-2-hydroxy-1-m-tolylethyl]-4-isopropylbenzamide | 482.23 | 1.42 | A |
| 128 | N-[2-(1-Aminoisoquinolin-6-ylcarbamoyl)-1-(3-ethoxyphenyl)-2-hydroxyethyl]-4-isopropylbenzamide | 512.24 | 1.43 | A |
| 129 | N-[2-(1-Aminoisoquinolin-6-ylcarbamoyl)-2-hydroxy-1-(4-isopropylphenyl)ethyl]-4-diethylaminobenzamide | 539.29 | 1.32 | A |
| 130 | N-[2-(1-Aminoisoquinolin-6-ylcarbamoyl)-1-(2-chlorophenyl)-2-hydroxyethyl]-4-diethylaminobenzamide | 531.2 | 1.16 | A |
| 131 | N-[2-(1-Aminoisoquinolin-6-ylcarbamoyl)-2-hydroxy-1-(4-trifluoromethylphenyl)ethyl]-4-diethylaminobenzamide | 565.23 | 1.26 | A |
| 132 | N-[2-(1-Aminoisoquinolin-6-ylcarbamoyl)-2-hydroxy-1-(4-trifluoromethylphenyl)ethyl]-4-isopropylbenzamide | 536.2 | 1.83 | B |
| 133 | N-[2-(1-Aminoisoquinolin-6-ylcarbamoyl)-1-(4-bromophenyl)-2-hydroxyethyl]-4-ethylbenzamide | 532.11 | 1.62 | C |
| 134 | N-[2-(2-Amino-3H-benzimidazol-5-ylcarbamoyl)-1-(3,5-dimethoxyphenyl)-2-hydroxyethyl]-4-isopropylbenzamide | 518.22 | 1.43 | A |
| 135 | N-[2-(2-Amino-3H-benzimidazol-5-ylcarbamoyl)-1-(3,5-dimethoxyphenyl)-2-hydroxyethyl]-4-diethylaminobenzamide | 547.26 | 1.05 | A |
| 136 | N-[2-(1-Aminoisoquinolin-6-ylcarbamoyl)-2-hydroxy-1-phenylethyl]-4-propylbenzamide | 468.22 | 1.36 | A |
| 137 | N-[2-(2-Amino-3H-benzimidazol-5-ylcarbamoyl)-1-(2-chlorophenyl)-2-hydroxyethyl]-4-isopropylbenzamide | 491.17 | 1.35 | A |
| 138 | N-[2-(1-Aminoisoquinolin-6-ylcarbamoyl)-2-hydroxy-1-phenylethyl]-4-cyclopropylbenzamide | 466.2 | 1.45 | B |
| 139 | N-[2-(1-Aminoisoquinolin-6-ylcarbamoyl)-1-(2-chlorophenyl)-2-hydroxyethyl]-4-ethylbenzamide | 488.16 | 1.53 | B |
| 140 | N-[2-(2-Aminobenzothiazol-6-ylcarbamoyl)-1-furan-2-yl-2-hydroxyethyl]-4-diethylaminobenzamide | 493.18 | 1.03 | B |
| 141 | N-[2-(2-Amino-3H-benzimidazol-5-ylcarbamoyl)-1-(2-fluorophenyl)-2-hydroxyethyl]-4-diethylaminobenzamide | 504.23 | 1.04 | A |

TABLE 1-continued

| Example No. | Compound | Mass from LC-MS | $R_t$ from LC-MS | LC-MS method |
|---|---|---|---|---|
| 142 | N-[2-(2-Amino-3H-benzimidazol-5-ylcarbamoyl)-1-(3,5-difluorophenyl)-2-hydroxyethyl]-4-isopropyl-benzamide | 493.19 | 1.58 | B |
| 143 | N-[2-(2-Amino-3H-benzimidazol-5-ylcarbamoyl)-1-(3,5-difluorophenyl)-2-hydroxyethyl]-4-diethyl-aminobenzamide | 522.22 | 1.21 | B |
| 144 | N-[2-(2-Amino-3H-benzimidazol-5-ylcarbamoyl)-1-(5-fluoro-2-methanesulfonylphenyl)-2-hydroxy-ethyl]-4-diethylaminobenzamide | 582.21 | 1.36 | A |
| 145 | N-[2-(2-Amino-3H-benzimidazol-5-ylcarbamoyl)-1-(5-fluoro-2-methanesulfonylphenyl)-2-hydroxy-ethyl]-4-diethylaminobenzamide | 553.18 | 1.54 | A |
| 146 | N-[2-(2-Amino-3H-benzimidazol-5-ylcarbamoyl)-1-(3-chlorophenyl)-2-hydroxyethyl]-4-diethyl-aminobenzamide | 491.17 | 1.6 | A |
| 147 | N-[2-(2-Amino-3H-benzimidazol-5-ylcarbamoyl)-1-(3-chlorophenyl)-2-hydroxyethyl]-4-diethyl-aminobenzamide | 520.2 | 1.43 | A |
| 148 | N-[2-(2-Amino-3H-benzimidazol-5-ylcarbamoyl)-2-hydroxy-1-(2-trifluoromethoxyphenyl)ethyl]-4-iso-propylbenzamide | 541.19 | 1.6 | A |
| 149 | N-[2-(2-Amino-3H-benzimidazol-5-ylcarbamoyl)-2-hydroxy-1-(2-trifluoromethoxyphenyl)ethyl]-4-diethylaminobenzamide | 570.22 | 1.47 | A |
| 150 | N-[2-(2-Amino-3H-benzimidazol-5-ylcarbamoyl)-2-hydroxy-1-o-tolylethyl]-4-diethylaminobenzamide | M + 1 = 512 | 0.93 | D |
| 151 | N-[2-(2-Amino-3H-benzimidazol-5-ylcarbamoyl)-2-hydroxy-1-thiophen-2-ylethyl]-4-diethylamino-benzamide | 509.16 | 1.08 | A |
| 152 | 9H-Fluoren-9-ylmethyl [(1S,2R)-2-(2-amino-3H-benzimidazol-5-ylcarbamoyl)-2-hydroxy-1-phenyl-ethyl]carbamate | 534.41 | 1.47 | A |
| 153 | 2-Chlorobenzyl [2-(2-amino-3H-benzimidazol-5-yl-carbamoyl)-2-hydroxy-1-phenylethyl]carbamate | 480.19 | 1.26 | A |

Pharmacological Examples

Factor IXa Determination Method

The prepared substances from the examples were tested for inhibition of the enzymatic activity of FIXa using the substrate PEFA 3107 (Pentapharm/Loxo; via S. Black GmbH, Baumstrasse 41, 47198 Duisburg, Germany; Pr. No. 095-20) and factor IXa (Calbiochem, Merck KGaA markets Calbiochem in Germany, Life Science & Analytics, 64293 Darmstadt; Pr. No. 233290). In this method, 28 µl of test buffer (50 mM α,α,α-tris(hydroxymethyl)methylamine (TRIS), 100 mM NaCl, 5 mM $CaCl_2$, 0.1% bovine serum albumin, pH 7.4) and 10 µl of factor IXa (277 nM final concentration in the test batch) were added to 2 µl of 10 mM dimethyl sulfoxide solution of the respective test substance, and the mixture was incubated for 15 minutes at room temperature in a 96 half-well microtiter plate. The enzyme reaction was started by addition of 10 µl of substrate (1 mM stock solution in water). The time course of the reaction was monitored at 405 nm in a microtiter plate reader (SpectraMax plus 384; Molecular Devices) for 15 minutes.

The $IC_{50}$ was calculated from the averaged values (duplicate determination) of a dilution series of the test substance with the aid of the software Grafit 4 (Erithacus Software, UK). The inhibition constants ($K_i$) were calculated according to the Cheng Prusoff equation $Ki=IC_{50}/(1+(S/Km))$, where S=concentration of the test substrate in the test and $K_m$=Michaelis-Menten constant.

Table 2 shows the results.

TABLE 2

| Compound from Example | Factor IXa enzyme assay $IC_{50}$ [micro M] |
|---|---|
| 17 | 0.28 |
| 53 | 1.34 |
| 68 | 0.73 |
| 81 | 0.57 |
| 87 | 0.14 |
| 134 | 0.17 |

What is claimed is:
1. A compound of formula I

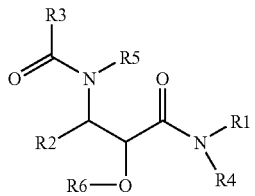

or a stereoisomeric form of a compound of formula I, or a mixture of such forms in any ratio, or a physiologically tolerable salt of a compound of formula I, where
R1 is
1) —($C_6$-$C_{14}$)-aryl-Z, in which Z is a basic nitrogen-containing group and in which aryl is unsubstituted or mono-, di- or trisubstituted by T, 2) —($C_3$-$C_{12}$)-cycloalkyl-Z, in which Z is a basic nitrogen-containing group and in which cycloalkyl is unsubstituted or mono-, di- or trisubstituted by T,
3) a four- to fifteen-membered Het-Z, in which Z is a basic nitrogen-containing group and in which Het is unsubstituted or additionally mono-, di- or trisubstituted by T, R2 is
1) —($C_0$-$C_4$)-alkylene-($C_6$-$C_{14}$)-aryl, in which aryl is unsubstituted or mono-, di- or trisubstituted by T,
2) —($C_0$-$C_4$)-alkylene-($C_3$-$C_8$)-cycloalkyl, in which cycloalkyl is unsubstituted or mono-, di- or trisubstituted by T, or
3) —($C_0$-$C_4$)-alkylene-Het, in which Het is unsubstituted or mono-, di- or trisubstituted by T, R3 is
1) —($C_0$-$C_4$)-alkylene-($C_6$-$C_{14}$)-aryl, in which aryl is unsubstituted or mono-, di- or trisubstituted by T,
2) —O—($C_1$-$C_4$)-alkylene-($C_6$-$C_{14}$)-aryl, in which aryl is unsubstituted or mono-, di- or trisubstituted by T,
3) —($C_0$-$C_4$)-alkylene-Het, in which Het is unsubstituted or mono-, di- or trisubstituted by T,
4) —O—($C_1$-$C_4$)-alkylene-Het, in which Het is unsubstituted or mono-, di- or trisubstituted by T,
5) —($C_0$-$C_4$)-alkylene-($C_6$-$C_{14}$)-aryl-Q-($C_6$-$C_{14}$)-aryl, in which the two aryl radicals in each case independently of one another are unsubstituted or mono-, di- or trisubstituted by T,
6) —($C_0$-$C_4$)-alkylene-($C_6$-$C_{14}$)-aryl-Q-($C_3$-$C_{12}$)-cycloalkyl, in which aryl and cycloalkyl in each case independently of one another are unsubstituted or mono-, di- or trisubstituted by T,
7) —($C_0$-$C_4$)-alkylene-($C_6$-$C_{14}$)-aryl-Q-Het, in which aryl and Het in each case independently of one another are unsubstituted or mono-, di- or trisubstituted by T,
8) —($C_0$-$C_4$)-alkylene-Het-Q-($C_6$-$C_{14}$)-aryl, in which aryl and Het in each case independently of one another are unsubstituted or mono-, di- or trisubstituted by T, or
9) —($C_0$-$C_4$)-alkylene-Het-Q-Het, in which the two Het radicals in each case independently of one another are unsubstituted or mono-, di- or trisubstituted by T,
10) —N(R5)—($C_1$-$C_4$)-alkylene-($C_6$-$C_{14}$)-aryl, in which aryl is unsubstituted or mono-, di- or trisubstituted by T, or
11) —N(R5)—($C_1$-$C_4$)-alkylene-Het, in which Het is unsubstituted or mono-, di- or trisubstituted by T, Q is a covalent bond, —($C_1$-$C_4$)-alkylene, —NH—, —N(($C_1$-$C_4$)-alkyl)-, —O—, —S—, or —$SO_2$—, T is
1) halogen,
2) —($C_1$-$C_6$)-alkyl, in which alkyl is unsubstituted or mono-, di- or trisubstituted by —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_8$)-cycloalkyl,
5) —OH,
6) —O—($C_1$-$C_4$)-alkyl,
7) —O—($C_1$-$C_3$)-fluoroalkyl,
8) —$NO_2$,
9) —CN,
10) —N(R10)(R11), in which R10 and R11 independently of one another are a hydrogen atom, —($C_3$-$C_9$)-cycloalkyl, halogen or —($C_1$-$C_6$)-alkyl,
11) —C(O)—NH—R10,
12) —NH—C(O)—R10,
13) —NH—$SO_2$—R10,
14) —$SO_2$—($C_1$-$C_4$)-alkyl,
15) —$SO_2$—NH—R10,
16) —$SO_2$—($C_1$-$C_3$)-fluoroalkyl,
17) —S—($C_1$-$C_4$)-alkyl or
18) —S—($C_1$-$C_3$)-fluoroalkyl, R4 and R5 are identical or different and independently of one another are a hydrogen atom or —($C_1$-$C_4$)-alkyl, and R6 is a hydrogen atom, —C(O)—R12, —C(O)—O—R12, —C(O)—NH—R12 or —($C_1$-$C_4$)-alkyl, where R12 is —($C_1$-$C_6$)-alkyl, —($C_3$-$C_9$)-cycloalkyl, —($C_6$-$C_{14}$)-aryl or Het.

2. A compound of formula I as claimed in claim 1, where R1 is
1) —($C_6$-$C_{14}$)-aryl-Z, where aryl is selected from the group consisting of phenyl and naphthyl, and in which aryl is unsubstituted or mono-, di- or trisubstituted by T and Z is amino, amidino, aminomethylene, aminopyridinyl, azetidinyl, guanidino, piperidinyl, pyridinyl or pyrrolidinyl, or
2) a four- to fifteen-membered Het-Z, where Het is selected from the group consisting of acridinyl, azepinyl, azetidinyl, benzimidazolinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, beta-carbolinyl, quinazolinyl, quinolinyl, quinolizinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl or xanthenyl and in which Het is unsubstituted or mono-, di- or trisubstituted by T and in which Z is as defined above, R2 is
1) —($C_0$-$C_4$)-alkylene-($C_6$-$C_{14}$)-aryl, in which aryl is as defined above and is unsubstituted or mono-, di- or trisubstituted by T, 2) —(C₀-C₄)-alkylene-(C₃-C₈)-cycloalkyl, in which cycloalkyl is unsubstituted or mono-, di- or trisubstituted by T, or
3) —(C₀-C₄)-alkylene-Het, in which Het is as defined above and is unsubstituted or mono-, di- or trisubstituted by T, R3 is
1) —(C₀-C₄)-alkylene-(C₆-C₁₄)-aryl, in which aryl is as defined above and is unsubstituted or mono-, di- or trisubstituted by T,
2) —(C₀-C₄)-alkylene-Het, in which Het is as defined above and is unsubstituted or mono-, di- or trisubstituted by T,
3) —(C₀-C₄)-alkylene-(C₆-C₁₄)-aryl-Q-(C₆-C₁₄)-aryl, in which the two aryls in each case independently of one another are as defined above and in each case independently of one another are unsubstituted or mono-, di- or trisubstituted by T,
4) —(C₀-C₄)-alkylene-(C₆-C₁₄)-aryl-Q-(C₃-C₁₂)-cycloalkyl, in which aryl is as defined above and cycloalkyl is unsubstituted or mono-, di- or trisubstituted by T,
5) —(C₀-C₄)-alkylene-(C₆-C₁₄)-aryl-Q-Het, in which aryl and Het are as defined above and in each case independently of one another are unsubstituted or mono-, di- or trisubstituted by T,
6) —(C₀-C₄)-alkylene-Het-Q-(C₆-C₁₄)-aryl, in which aryl and Het are as defined above and in each case independently of one another are unsubstituted or mono-, di- or trisubstituted by T, or
7) —(C₀-C₄)-alkylene-Het-Q-Het, in which the two Het radicals are as defined above and in each case independently of one another are unsubstituted or mono-, di- or trisubstituted by T, Q is a covalent bond, —(C₁-C₄)-alkylene, —NH—, —N((C₁-C₄)-alkyl)- or —O—, T is
1) halogen,
2) —(C₁-C₆)-alkyl, in which alkyl is unsubstituted or mono-, di- or trisubstituted by —(C₁-C₃)-fluoroalkyl, —N—C(O)—OH or —N—C(O)—(C₁-C₄)-alkyl,
3) —(C₁-C₃)-fluoroalkyl,
4) —(C₃-C₆)-cycloalkyl,
5) —OH,
6) —O—(C₁-C₄)-alkyl,
7) —O—(C₁-C₃)-fluoroalkyl,
8) —NO₂,
9) —CN,
10) —N(R10)(R11), in which R10 and R11 independently of one another are a hydrogen atom, —(C₃-C₆)-cycloalkyl, halogen or —(C₁-C₆)-alkyl,
11) —C(O)—NH—R10,
12) —NH—C(O)—R10,
13) —NH—SO₂—R10,
14) —SO₂—(C₁-C₄)-alkyl,
15) —SO₂—NH—R10,
16) —SO₂—(C₁-C₃)-fluoroalkyl,
17) —S—(C₁-C₄)-alkyl or
18) —S—(C₁-C₃)-fluoroalkyl, R4 and R5 are identical or different and independently of one another are a hydrogen atom or —(C₁-C₄)-alkyl, and
R6 is a hydrogen atom, —C(O)—R12, —C(O)—O—R12, —C(O)—NH—R12 or —(C₁-C₄)-alkyl, where R12 is —(C₁-C₆)-alkyl, —(C₃-C₆)-cycloalkyl, —(C₆-C₁₄)-aryl or Het.

3. A compound of formula I as claimed in claim 2, where
R1 is 4-benzamidine, aminomethylphenyl or Het-Z, where Het is selected from the group consisting of benzimidazolyl, benzothiazolyl and isoquinolinyl, and in which Z is amino,
R2 is
1) phenyl, in which phenyl is unsubstituted or mono- or disubstituted by T, or
2) Het-1, in which Het-1 is selected from the group consisting of furanyl, pyrazolyl or thienyl and Het-1 is unsubstituted or mono- or disubstituted by T,
R3 is
1) phenyl, in which phenyl is unsubstituted or mono- or disubstituted by T,
2) Het-2, in which Het-2 is selected from the group consisting of benzimidazolyl, benzofuranyl, benzothiophenyl, quinolinyl, quinoxalinyl, furanyl, indolyl, isoquinolinyl, isoxazolyl, morpholinyl, piperidinyl, pyridyl, pyrimidinyl, pyrrolidinyl, pyrrolyl, thienyl, thienopyrrolyl or thienothiophenyl and in which Het-2 is unsubstituted or mono- or disubstituted by T,
3)-phenyl-Q-phenyl, in which the two phenyl radicals in each case independently of one another are unsubstituted or mono- or disubstituted by T,
4) phenyl-Q-(C₃-C₆)-cycloalkyl, in which phenyl and cycloalkyl in each case independently of one another are unsubstituted or mono- or disubstituted by T,
5) phenyl-Q-Het-2, in which Het-2 is as defined above and phenyl and Het-2 in each case independently of one another are unsubstituted or mono- or disubstituted by T,
6) Het-2-Q-phenyl, in which Het-2 is as defined above and phenyl and Het-2 in each case independently of one another are unsubstituted or mono- or disubstituted by T, or
7) Het-2-Q-Het-2, in which the two Het-2 radicals are as defined above and in each case independently of one another are unsubstituted or mono- or disubstituted by T, Q is a covalent bond, —CH₂—, —N(CH₃)— or —O—, T is
1) F, Cl or Br,
2) —(C₁-C₄)-alkyl, in which alkyl is unsubstituted or mono- or disubstituted by —CF₃ or —N—C(O)—CH₃,
3) —CF₃,
4) —O—(C₁-C₄)-alkyl,
5) —O—CF₃,
6) —NO₂,
7) —N(R10)(R11), in which R10 and R11 independently of one another are a hydrogen atom or —(C₁-C₄)-alkyl,
8) —SO₂—CH₃,
9) —S—CF₃ or
10) —S—(C₁-C₂)-alkyl, R4, R5 and R6 are in each case a hydrogen atom.

4. A compound of formula I as claimed in claim 3, which is the compound N-[(1S,2R)-2-(1-aminoisoquinolin-7-ylcarbamoyl)-2-hydroxy-1-phenylethyl]-4-tert-butylbenzamide, N-[(1S,2R)-2-(1-aminoisoquinolin-6-ylcarbamoyl)-2-hydroxy-1-phenylethyl]-4-diethylaminobenzamide, N-[(1S,2R)-2-(2-aminobenzothiazol-6-ylcarbamoyl)-2-hydroxy-1-phenylethyl]-4-isopropylbenzamide, N-[(1R,2R)-2-(1-aminoisoquinolin-6-ylcarbamoyl)-1-furan-2-yl-2-hydroxyethyl]-4-diethylaminobenzamide, N-[(1S,2R)-2-(2-aminobenzothiazol-6-ylcarbamoyl)-1-(2-chlorophenyl)-2- hydroxyethyl]-4-isopropylbenzamide, N-[(1S,2R)-2-(2-amino-3H-benzimidazol-5-ylcarbamoyl)-1-(2-fluorophenyl)-2-hydroxyethyl]-4-isopropylbenzamide, N-[(1S,2R)-[2-(2-amino-3H-benzimidazol-5-ylcarbamoyl)-2-hydroxy-1-phenylethyl]-4-tertiary-butylbenzamide, N-[(1S,2R)-2-(4-aminomethylphenylcarbamoyl)-2-hydroxy-1-phenylethyl]benzamide, N-[(1S,2R)-2-(2,4-diaminoquinazolin-6-ylcarbamoyl)-2-hydroxy-1-phenylethyl]benzamide, 4-amino-N-[2-(2-amino-3H-benzimidazol-5-ylcarbamoyl)-2-hydroxy-1-phenylethyl]benzamide, quinoxaline-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-methoxybenzamide, thiophene-3-carboxylic acid [2-(2-amino-3H-benzimidazol-5-ylcarbamoyl)-2-hydroxy-1-phenylethyl]amide, 1-methyl-1H-pyrrole-2-carboxylic acid [(1S,2R)-2-(2-amino-3H-benzimidazol-5-ylcarbamoyl)-2-hydroxy-1-phenylethyl]amide, quinoline-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-cyclohexylbenzamide, N-[2-(2-amino-3H-benzimidazol-5-ylcarbamoyl)-2-hydroxy-1-phenylethyl]-4-isopropylbenzamide, N-[2-(2-amino-3H-benzimidazol-5-ylcarbamoyl)-2-hydroxy-1-phenylethyl]-4-trifluoromethoxy-benzamide, N-[2-(2-amino-3H-benzimidazol-5-ylcarbamoyl)-2-hydroxy-1-phenylethyl]-4-diethylaminobenzamide, N-[2-(2-amino-3H-benzimidazol-5-ylcarbamoyl)-2-hydroxy-1-phenylethyl]-4-phenoxybenzamide, N-[2-(2-amino-3H-benzimidazol-5-ylcarbamoyl)-2-hydroxy-1-phenylethyl]-4-benzylbenzamide, N-[2-(2-amino-3H-benzimidazol-5-ylcarbamoyl)-2-hydroxy-1-phenylethyl]-4-isopropoxybenzamide, N-[2-(2-amino-3H-benzimidazol-5-ylcarbamoyl)-2-hydroxy-1-phenylethyl]-4-methylsulfanylbenzamide, N-[2-(2-amino-3H-benzimidazol-5-ylcarbamoyl)-2-hydroxy-1-phenylethyl]-4-ethylsulfanylbenzamide, N-[2-(2-amino-3H-benzimidazol-5-ylcarbamoyl)-2-hydroxy-1-phenylethyl]-4-[(4,6-dimethylpyrimidin-2-yl)methyl-amino]benzamide, N-[2-(2-amino-3H-benzimidazol-5-ylcarbamoyl)-2-hydroxy-1-phenylethyl]-4-pyridin-3-ylbenzamide, 4-(2-acetylamino-3,3,3-trifluoro-propyl)-N-[2-(2-amino-3H-benzimidazol-5-ylcarbamoyl)-2-hydroxy-1-phenylethyl]benzamide, 1-methyl-1H-indole-2-carboxylic acid [2-(2-amino-3H-benzimidazol-5-ylcarbamoyl)-2-hydroxy-1-phenylethyl]amide, 5-methoxy-1H-indole-2-carboxylic acid [2-(2-amino-3H-benzimidazol-5-ylcarbamoyl)-2-hydroxy-1-phenylethyl]amide, 5-ethyl-1H-indole-2-carboxylic acid [2-(2-amino-3H-benzimidazol-5-ylcarbamoyl)-2-hydroxy-1-phenylethyl]amide, 6-methoxy-1H-indole-2-carboxylic acid [2-(2-amino-3H-benzimidazol-5-ylcarbamoyl)-2-hydroxy-1-phenylethyl]amide, 4-methoxyquinoline-2-carboxylic acid [2-(2-amino-3H-benzimidazol-5-ylcarbamoyl)-2-hydroxy-1-phenylethyl]amide, 3-ethoxyquinoxaline-2-carboxylic acid [2-(2-amino-3H-benzimidazol-5-ylcarbamoyl)-2-hydroxy-1-phenylethyl]amide, naphthalene-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-pyrrol-1-ylbenzamide, N-[2-(2-amino-3H-benzimidazol-5-ylcarbamoyl)-2-hydroxy-1-phenylethyl]-4-trifluoromethylsulfanylbenzamide, biphenyl-4-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-(2,2,2-trifluoroethoxy)benzamide, benzyl[2-(2-amino-3H-benzimidazol-5-ylcarbamoyl)-2-hydroxy-1-phenylethyl]carbamate, N-[2-(2-amino-3H-benzimidazol-5-ylcarbamoyl)-2-hydroxy-1-phenylethyl]-4-ethyl benzamide, N-[2-(2-amino-3H-benzimidazol-5-ylcarbamoyl)-2-hydroxy-1-phenylethyl]-4-ethoxybenzamide, 5-butylpyridine-2-carboxylic acid [2-(2-amino-3H-benzimidazol-5-ylcarbamoyl)-2-hydroxy-1-phenylethyl]amide, benzo[b]thiophene-2-carboxylic acid [2-(2-amino-3H-benzimidazol-5-ylcarbamoyl)-2-hydroxy-1-phenylethyl]amide, 6-methoxynaphthalene-2-carboxylic acid [2-(2-amino-3H-benzimidazol-5-ylcarbamoyl)-2-hydroxy-1-phenylethyl]amide, 4-(2,2,2-trifluoroethyl)-4H-thieno[3,2-b]pyrrole-5-carboxylic acid [2-(2-amino-3H-benzimidazol-5-ylcarbamoyl)-2-hydroxy-1-phenylethyl]amide, biphenyl-3,4'-dicarboxylic acid 4'-{[2-(2-amino-3H-benzimidazol-5-ylcarbamoyl)-2-hydroxy-1-phenylethyl]amide}3-methylamide, N-[2-(1-aminoisoquinolin-7-ylcarbamoyl)-2-hydroxy-1-phenylethyl]-4-diethylaminobenzamide, N-[2-(1-aminoisoquinolin-7-ylcarbamoyl)-2-hydroxy-1-phenylethyl]-4-isopropylbenzamide, N-[2-(1-aminoisoquinolin-7-ylcarbamoyl)-2-hydroxy-1-phenylethyl]-6-pyrrolidin-1-ylnicotinamide, N-[2-(1-aminoisoquinolin-7-ylcarbamoyl)-2-hydroxy-1-phenylethyl]-4-morpholin-4-ylbenzamide, N-[2-(1-aminoisoquinolin-7-ylcarbamoyl)-2-hydroxy-1-phenylethyl]-4-pyrrol-1-ylbenzamide, 1-ethyl-2,3-dimethyl-1H-indole-5-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-morpholin-4-ylbenzamide, N-[2-(1-aminoisoquinolin-7-ylcarbamoyl)-2-hydroxy-1-phenylethyl]-4-pyrrolidin-1-ylbenzamide, N-[2-(1-aminoisoquinolin-7-ylcarbamoyl)-2-hydroxy-1-phenylethyl]-6-morpholin-4-yl-nicotinamide, 5,6-dimethoxy-1H-indole-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-pyrrolidin-1-ylbenzamide, N-[2-(2-amino-3H-benzimidazol-5-ylcarbamoyl)-2-hydroxy-1-phenylethyl]-4-isobutylbenzamide, N-[2-(2-amino-3H-benzimidazol-5-ylcarbamoyl)-2-hydroxy-1-phenylethyl]-4-butylbenzamide, N-[2-(2-amino-3H-benzimidazol-5-ylcarbamoyl)-2-hydroxy-1-phenylethyl]-4-propylbenzamide, 4H-thieno[3,2-b]pyrrole-5-carboxylic acid [2-(2-amino-3H-benzimidazol-5-ylcarbamoyl)-2-hydroxy-1-phenylethyl]amide, N-[2-(4-carbamimidoyl-phenylcarbamoyl)-2-hydroxy-1-phenylethyl]-4-diethylaminobenzamide, 5-methoxy-1H-indole-2-carboxylic acid [2-(1-aminoisoquinolin-7-ylcarbamoyl)-2-hydroxy-1-phenylethyl]amide, 5-ethylthiophene-2-carboxylic acid [2-(1-aminoiso quinolin-7-ylcarbamoyl)-2-hydroxy-1-phenylethyl]amide, 5-tert-butyl-thiophene-2-carboxylic acid [2-(1-aminoisoquinolin-7-ylcarbamoyl)-2-hydroxy-1-phenylethyl]amide, N-[2-(1-aminoisoquinolin-6-ylcarbamoyl)-2-hydroxy-1-phenylethyl]benzamide, 6-bromobenzofuran-2-carboxylic acid [2-(2-amino-3H-benzimidazol-5-ylcarbamoyl)-2-hydroxy-1-phenylethyl]amide, 5-ethylthiophene-2-carboxylic acid [2-(2-amino-3H-benzimidazol-5-ylcarbamoyl)-2-hydroxy-1-phenylethyl]amide, thieno[3,2-b]thiophene-2-carboxylic acid [2-(2-amino-3H-benzimidazol-5-ylcarbamoyl)-2-hydroxy-1-phenylethyl]amide, 5-methoxybenzofuran-2-carboxylic acid [2-(2-amino-3H-benzimidazol-5-ylcarbamoyl)-2-hydroxy-1-phenylethyl]amide, benzo[b]thiophene-3-carboxylic acid [2-(2-amino-3H-benzimidazol-5-ylcarbamoyl)-2-hydroxy-1-phenylethyl]amide, 4-methylthiophene-2-carboxylic acid [2-(2-amino-3H-benzimidazol-5-ylcarbamoyl)-2-hydroxy-1- phenylethyl]amide, N-[2-(2-aminobenzothiazol-6-ylcarbamoyl)-2-hydroxy-1-phenylethyl]-4-diethylaminobenzamide, 1H-indole-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-dimethylaminobenzamide, 5-tert-butylthiophene-2-carboxylic acid [2-(2-amino-3H-benzimidazol-5-ylcarbamoyl)-2-hydroxy-1-phenylethyl]amide, N-[2-(2-amino-3H-benzimidazol-5-ylcarbamoyl)-2-hydroxy-1-phenylethyl]-4-methoxy-3-methylbenzamide, N-[2-(2-amino-3H-benzimidazol-5-ylcarbamoyl)-2-hydroxy-1-phenylethyl]-3-fluoro-4-methylbenzamide, 5-isopropylthiophene-3-carboxylic acid [2-(2-amino-3H-benzimidazol-5-ylcarbamoyl)-2-hydroxy-1-phenylethyl]amide, 5-ethylthiophene-3-carboxylic acid [2-(2-amino-3H-benzimidazol-5-ylcarbamoyl)-2-hydroxy-1-phenylethyl]amide, [2,2']bithiophenyl-5-carboxylic acid [2-(2-amino-3H-benzimidazol-5-ylcarbamoyl)-2-hydroxy-1-phenylethyl]amide, 5-methoxy-1H-indole-2-carboxylic acid [2-(1-aminoisoquinolin-6-ylcarbamoyl)-2-hydroxy-1-phenylethyl]amide, N-[2-(1-aminoisoquinolin-6-ylcarbamoyl)-2-hydroxy-1-phenylethyl]-4-methoxybenzamide, N-[2-(1-aminoisoquinolin-6-ylcarbamoyl)-2-hydroxy-1-phenylethyl]-4-isopropylbenzamide, N-[2-(1-aminoisoquinolin-6-ylcarbamoyl)-2-hydroxy-1-phenylethyl]-4-diethylaminobenzamide, N-[2-(1-aminoisoquinolin-6-ylcarbamoyl)-2-hydroxy-1-phenylethyl]-4-ethoxybenzamide, N-[2-(1-aminoisoquinolin-6-ylcarbamoyl)-2-hydroxy-1-phenylethyl]-4-ethylbenzamide, N-[2-(1-aminoisoquinolin-6-ylcarbamoyl)-2-hydroxy-1-phenylethyl]-4-tert-butylbenzamide, N-[2-(1-aminoisoquinolin-6-ylcarbamoyl)-2-hydroxy-1-phenylethyl]-3-dimethylaminobenzamide, N-[2-(1-aminoisoquinolin-6-ylcarbamoyl)-2-hydroxy-1-phenylethyl]-4-dimethylaminobenzamide, 5-ethylthiophene-2-carboxylic acid [2-(1-aminoisoquinolin-6-ylcarbamoyl)-2-hydroxy-1-phenylethyl]amide, 5-ethylthiophene-3-carboxylic acid [2-(1-aminoisoquinolin-6-ylcarbamoyl)-2-hydroxy-1-phenylethyl]amide, 5-tert-butyl-thiophene-2-carboxylic acid [2-(1-aminoisoquinolin-6-ylcarbamoyl)-2-hydroxy-1-phenylethyl]amide, N-[2-(1-aminoisoquinolin-6-ylcarbamoyl)-2-hydroxy-1-phenylethyl]-3-ethylbenzamide, N-[2-(1-aminoisoquinolin-6-ylcarbamoyl)-2-hydroxy-1-phenylethyl]-3-ethoxybenzamide, N-[2-(2-amino-1H-benzimidazol-5-yl carbamoyl)-2-hydroxy-1-(3-trifluoromethyl phenyl)ethyl]-4-isopropylbenzamide, N-[2-(2-amino-1H-benzimidazol-5-ylcarbamoyl)-2-hydroxy-1-(2-methoxyphenyl)ethyl]-4-isopropylbenzamide, N-[2-(2-amino-1H-benzimidazol-5-ylcarbamoyl)-2-hydroxy-1-(3-trifluoromethyl phenyl)ethyl]-4-diethylaminobenzamide, N-[2-(2-amino-1H-benzimidazol-5-ylcarbamoyl)-2-hydroxy-1-(2-methoxyphenyl)ethyl]-4-diethylaminobenzamide, N-[2-(2-amino-1H-benzimidazol-5-ylcarbamoyl)-2-hydroxy-1-(4-methoxyphenyl)ethyl]-4-diethylaminobenzamide, N-[2-(1-aminoisoquinolin-6-ylcarbamoyl)-1-(3-ethoxy-phenyl)-2-hydroxyethyl]-4-diethylaminobenzamide, N-[2-(2-amino-3H-benzimidazol-5-ylcarbamoyl)-2-hydroxy-1-(4-isopropylphenyl)ethyl]-4-diethylaminobenzamide, N-[2-(2-amino-3H-benzimidazol-5-ylcarbamoyl)-1-(3-ethoxyphenyl)-2-hydroxyethyl]-4-isopropylbenzamide, N-[2-(2-amino-3H-benzimidazol-5-ylcarbamoyl)-1-(3-ethoxyphenyl)-2-hydroxyethyl]-4-diethylaminobenzamide, N-[2-(1-aminoisoquinolin-6-ylcarbamoyl)-2-hydroxy-1-m-tolylethyl]-4-diethylaminobenzamide, N-[2-(2-amino-3H-benzimidazol-5-ylcarbamoyl)-2-hydroxy-1-(4-isopropylphenyl)ethyl]-4-isopropylbenzamide, N-[2-(2-aminobenzothiazol-6-ylcarbamoyl)-2-hydroxy-1-(4-trifluoromethylphenyl)ethyl]-4-isopropylbenzamide, N-[2-(2-aminobenzothiazol-6-ylcarbamoyl)-2-hydroxy-1-m-tolylethyl]-4-diethylaminobenzamide, N-[2-(2-aminobenzothiazol-6-ylcarbamoyl)-2-hydroxy-1-m-tolylethyl]-4-isopropylbenzamide, N-[2-(2-aminobenzothiazol-6-ylcarbamoyl)-2-hydroxy-1-(4-isopropylphenyl)ethyl]-4-diethylaminobenzamide, N-[2-(2-aminobenzothiazol-6-ylcarbamoyl)-1-(3-ethoxyphenyl)-2-hydroxyethyl]-4-diethylaminobenzamide, N-[2-(2-aminobenzothiazol-6-ylcarbamoyl)-2-hydroxy-1-(4-trifluoromethylphenyl)ethyl]-4-diethylaminobenzamide, N-[2-(2-amino-3H-benzimidazol-5-ylcarbamoyl)-1-(2-chlorophenyl)-2-hydroxyethyl]-4-diethylaminobenzamide, N-[2-(2-amino-3H-benzimidazol-5-ylcarbamoyl)-2-hydroxy-1-(4-trifluoromethylphenyl)ethyl]-4-isopropylbenzamide, N-[2-(2-amino-3H-benzimidazol-5-ylcarbamoyl)-2-hydroxy-1-(4-trifluoromethylphenyl)-ethyl]-4-diethylaminobenzamide, N-[2-(2-aminobenzothiazol-6-ylcarbamoyl)-1-(3-ethoxyphenyl)-2-hydroxyethyl]-4-isopropylbenzamide, N-[2-(2-aminobenzothiazol-6-ylcarbamoyl)-1-(2-chlorophenyl)-2-hydroxyethyl]-4-diethylaminobenzamide, N-[2-(1-aminoisoquinolin-6-ylcarbamoyl)-1-(3-bromo-phenyl)-2-hydroxyethyl]-4-diethylaminobenzamide, N-[2-(1-aminoisoquinolin-6-ylcarbamoyl)-1-(3-bromophenyl)-2-hydroxyethyl]-4-ethylbenzamide, N-[2-(1-aminoisoquinolin-6-ylcarbamoyl)-2-hydroxy-1-(4-isopropylphenyl)ethyl]-4-isopropylbenzamide, N-[2-(1-aminoisoquinolin-6-ylcarbamoyl)-1-(2-chloro-phenyl)-2-hydroxyethyl]-4-isopropylbenzamide, N-[2-(2-amino-3H-benzimidazol-5-ylcarbamoyl)-2-hydroxy-1-m-tolylethyl]-4-isopropylbenzamide, N-[2-(2-amino-3H-benzimidazol-5-ylcarbamoyl)-2-hydroxy-1-m-tolylethyl]-4-diethylaminobenzamide, N-[2-(1-aminoisoquinolin-6-ylcarbamoyl)-1-(4-bromophenyl)-2-hydroxyethyl]-4-diethylaminobenzamide, N-[2-(1-aminoisoquinolin-6-ylcarbamoyl)-1-(4-bromophenyl)-2-hydroxyethyl]-4-isopropylbenzamide, N-[2-(1-aminoisoquinolin-6-ylcarbamoyl)-1-(3-bromophenyl)-2-hydroxyethyl]-4-isopropylbenzamide, N-[2-(1-aminoisoquinolin-6-ylcarbamoyl)-2-hydroxy-1-m-tolylethyl]-4-isopropylbenzamide, N-[2-(1-aminoisoquinolin-6-ylcarbamoyl)-1-(3-ethoxyphenyl)-2-hydroxyethyl]-4-isopropylbenzamide, N-[2-(1-aminoisoquinolin-6-ylcarbamoyl)-2-hydroxy-1-(4-isopropylphenyl)ethyl]-4-diethylaminobenzamide, N-[2-(1-aminoisoquinolin-6-ylcarbamoyl)-1-(2-chlorophenyl)-2-hydroxyethyl]-4-diethylaminobenzamide, N-[2-(1-aminoisoquinolin-6-ylcarbamoyl)-2-hydroxy-1-(4-trifluoromethylphenyl)-ethyl]-4-diethylaminobenzamide, N-[2-(1-aminoisoquinolin-6-ylcarbamoyl)-2-hydroxy-1-(4-trifluoromethylphenyl)ethyl]-4-isopropylbenzamide, N-[2-(1-aminoisoquinolin-6-ylcarbamoyl)-1-(4-bromophenyl)-2-hydroxyethyl]-4-ethyl benzamide, N-[2-(2-amino-3H-benzimidazol-5-ylcarbamoyl)-1-(3,5-dimethoxyphenyl)-2-hydroxyethyl]-4-isopropylbenzamide, N-[2-(2-amino-3H-benzimidazol-5-ylcarbamoyl)-1-(3,5-dimethoxyphenyl)-2-hydroxyethyl]-4-diethylaminobenzamide, N-[2-(1-aminoisoquinolin-6-ylcarbamoyl)-2-hydroxy-1-phenylethyl]-4-propylbenzamide, N-[2-(2-amino-3H-benzimidazol-5-ylcarbamoyl)-1-(2-chlorophenyl)-2-hydroxyethyl]-4-isopropylbenzamide, N-[2-(1-aminoisoquinolin-6-ylcarbamoyl)-2-hydroxy-1-phenylethyl]-4-cyclopropylbenzamide, N-[2-(1-aminoisoquinolin-6-ylcarbamoyl)-1-(2-chloro-phenyl)-2-hydroxyethyl]-4-ethylbenzamide, N-[2-(2-aminobenzothiazol-6-ylcarbamoyl)-1-furan-2-yl-2-hydroxyethyl]-4-diethylaminobenzamide, N-[2-(2-amino- 3H-benzimidazol-5-ylcarbamoyl)-1-(2-fluorophenyl)-2-hydroxyethyl]-4-diethylaminobenzamide, N-[2-(2-amino-3H-benzimidazol-5-ylcarbamoyl)-1-(3,5-difluorophenyl)-2-hydroxyethyl]-4-isopropylbenzamide, N-[2-(2-amino-3H-benzimidazol-5-ylcarbamoyl)-1-(3,5-difluorophenyl)-2-hydroxyethyl]-4-diethylaminobenzamide, N-[2-(2-amino-3H-benzimidazol-5-ylcarbamoyl)-1-(5-fluoro-2-methanesulfonylphenyl)-2-hydroxyethyl]-4-diethylaminobenzamide, N-[2-(2-amino-3H-benzimidazol-5-ylcarbamoyl)-1-(5-fluoro-2-methanesulfonylphenyl)-2-hydroxyethyl]-4-diethylaminobenzamide, N-[2-(2-amino-3H-benzimidazol-5-ylcarbamoyl)-1-(3-chlorophenyl)-2-hydroxyethyl]-4-diethylaminobenzamide, N-[2-(2-amino-3H-benzimidazol-5-ylcarbamoyl)-1-(3-chlorophenyl)-2-hydroxyethyl]-4-diethylaminobenzamide, N-[2-(2-amino-3H-benzimidazol-5-ylcarbamoyl)-2-hydroxy-1-(2-trifluoromethoxyphenyl)ethyl]-4-isopropylbenzamide, N-[2-(2-amino-3H-benzimidazol-5-ylcarbamoyl)-2-hydroxy-1-(2-trifluoromethoxyphenyl)ethyl]-4-diethylaminobenzamide, N-[2-(2-amino-3H-benzimidazol-5-ylcarbamoyl)-2-hydroxy-1-o-tolylethyl]-4-diethylaminobenzamide, N-[2-(2-amino-3H-benzimidazol-5-ylcarbamoyl)-2-hydroxy-1-thiophen-2-ylethyl]-4-diethylaminobenzamide, 9H-fluoren-9-ylmethyl[(1S,2R)-2-(2-amino-3H-benzimidazol-5-ylcarbamoyl)-2-hydroxy-1-phenylethyl]carbamate or 2-chlorobenzyl[2-(2-amino-3H-benzimidazol-5-ylcarbamoyl)-2-hydroxy-1-phenylethyl]carbamate.

5. A process for the preparation of a compound of formula I as claimed in claim 1, which comprises
   a) reacting a compound of the formula II

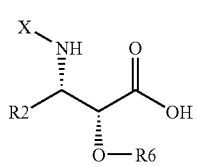

(II)

where X is an amino-protective group and the radicals R2 and R6 are as defined in formula I with a compound NH(R1)(R4) to give a compound of the formula III,

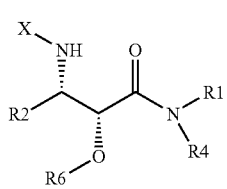

(III)

where X is an amino-protective group and the radicals R1, R2, R4 and R6 are as defined in formula I, and converting the compound of the formula III by removal of the protective group to a compound of the formula IV,

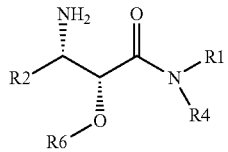

(IV)

where the radicals R1, R2, R4 and R6 are as defined in formula I, and reacting with the compound of the formula V

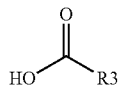

(V)

to give the compound of the formula I, or
   b) either isolating the compound of the formula I prepared according to process a) in free form or releasing it from physiologically intolerable salts or, in the case of the presence of acidic or basic groups, converting it into physiologically tolerable salts, or
   c) separating a compound of the formula I prepared according to process a), or a suitable precursor of the formula I which on account of its chemical structure occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

6. A medicament which comprises an efficacious amount of at least one compound of formula I as claimed in claim 1 in a pharmaceutically suitable and physiologically tolerable carrier.

7. A method for the therapy of a disease which accompanies thromboses, embolisms, hypercoagulability or fibrotic changes, the method comprising administering a pharmaceutically effective dose of a compound of formula I as claimed in claim 1.

8. The method as claimed in claim 7, wherein the disease is a myocardial infarct; angina pectoris; stroke; peripheral vascular disease; deep vein thrombosis; pulmonary embolism; an embolic or thrombotic event caused by cardiac arrhythmia, restenosis after revascularization, angioplasty, stent implantation or a bypass operation; thrombosis after a surgical intervention; sepsis; atherosclerosis; diabetes; rheumatoid arthritis; arthrosis; fibrin deposits; chronic obstructive pulmonary disease; adult respiratory distress syndrome; fibrin deposits in the eye after eye operations; or scar formation.

\* \* \* \* \*